US007863251B2

(12) United States Patent
Zhuo et al.

(10) Patent No.: US 7,863,251 B2
(45) Date of Patent: Jan. 4, 2011

(54) HEPATIC STELLATE CELL SPECIFIC PROMOTER AND USES THEREOF

(75) Inventors: Lang Zhuo, Singapore (SG); Gunter Maubach, Singapore (SG)

(73) Assignee: Agency for Science, Technology and Research, Centros (SG)

( * ) Notice: Subject to any disclaimer, the term of this patent is extended or adjusted under 35 U.S.C. 154(b) by 18 days.

(21) Appl. No.: 11/916,987

(22) PCT Filed: Jun. 9, 2006

(86) PCT No.: PCT/SG2006/000149

§ 371 (c)(1),
(2), (4) Date: Aug. 11, 2008

(87) PCT Pub. No.: WO2006/132606

PCT Pub. Date: Dec. 14, 2006

(65) Prior Publication Data

US 2009/0202502 A1 Aug. 13, 2009

Related U.S. Application Data

(60) Provisional application No. 60/688,733, filed on Jun. 9, 2005.

(51) Int. Cl.
*A61K 48/00* (2006.01)
*C07H 21/04* (2006.01)
*C12Q 1/68* (2006.01)

(52) U.S. Cl. ............................ 514/44; 435/6; 435/325; 435/375; 536/23.1; 536/24.5

(58) Field of Classification Search ....................... None
See application file for complete search history.

(56) References Cited

U.S. PATENT DOCUMENTS

| | | | | |
|---|---|---|---|---|
| 6,501,003 | B1 * | 12/2002 | Messing et al. | 800/18 |
| 6,506,559 | B1 | 1/2003 | Fire et al. | |
| 7,348,313 | B2 | 3/2008 | Poelstra et al. | |
| 2005/0227936 | A1 * | 10/2005 | McSwiggen et al. | 514/44 |
| 2007/0299029 | A1 * | 12/2007 | Zhuo et al. | 514/44 |
| 2009/0053295 | A1 | 2/2009 | Stout | |

OTHER PUBLICATIONS

Kinoshita et al. Hepatology v.38, Abstract 216; 2003.*

Dooley, Steven et al. Smad7 prevents activation of hepatic stellate cells and liver fibrosis in rats. Gastroenterology, vol. 125, No. 1, Jul. 2003, pp. 178-191.

Borkham-Kamphorst E. et al. Antisense strategy against PDGF B-chain proves effective in . . . Bloch. and Biophysical Research Comm., . . . vol. 321, No. 1, Aug. 20/04, pp. 413-423.

Friedman S.L. Molecular regulation of hepatic fibrosis an Integrated . . . J. of Biol. Chem., American Soc. of Biolochemical Biol. vol. 275, No. 4, Jan. 28/00, pp. 2247-2250.

Nakao Atsuhito et al. TGF-beta receptor mediated signalling through Smad2, Smad3 and Smad4 . EMBO, Journal, vol. 16, No. 17, 1997, pp. 5353-5362.

Hautekeete Marc. L. et al. The hepatic stellate (Ito) cell: Its role in human liver disease. Virchows Archiv., vol. 430, No. 3, 1997, pp. 195-207.

Extended European Search Report dated Apr. 24, 2009 , issued in European Application No. 06748100.2, 8 pages.

Chen and Zhang, "The antioxidant (-)-epigallocatechin-3-gallate inhibits rat hepatic stellate cell proliferation in vitro by blocking the tyrosine phosphorylation and reducing the gene expression of platelet-derived growth factor-beta receptor," *The Journal of Biological Chemistry*, 278(26):23381-23389, 2003.

Chen et al., "The antioxidant (-)-epigallocatechin-3-gallate inhibits activated hepatic stellate cell growth and suppresses acetaldehyde-induced gene expression," *Biochemical Journal*, 368(Pt 3):695-704, 2002.

Condorelli et al., "Tissue-specific DNA methylation patterns of the rat glial fibrillary acidic protein gene," *Journal of Neuroscience Research*, 39(6):694-707, 1994.

Dampier et al., "Differences between human breast cancer cell lines in susceptibility towards growth inhibition by genistein," *British Journal of Cancer*, 85(4):618-624, 2001.

Gonzalez Bosc et al., "Nuclear factor of activated T cells and serum response factor cooperatively regulate the activity of an alpha-actin intronic enhancer," *The Journal of Biological Chemistry*, 280(28):26113-26120, 2005.

Gopalan et al., "Astrocyte-specific expression of the alpha 1-antichymotrpsin and glial fibrillary acidic protein genes requires activator protein-1," *The Journal of Biological Chemistry*, 281(4):1956-1963, 2006.

Higashi et al., "Epigallocatechin-3-gallate, a green-tea polyphenol, suppresses Rho signalling in TWNT-4 human hepatic stellate cells," *The Journal of Laboratory and Clinical Medicine*, 145(6):316-332, 2005.

Houglum et al., "Two different cis-acting regulatory regions direct cell-specific transcription of the collagen alpha 1(I) gene in hepatic stellate cells and in skin and tendon fibroblasts," *The Journal of Clinical Investigation*, 96(5):2269-2276, 1995.

Kang et al., "Effect of genistein and quercetin on proliferation, collagen synthesis, and type I procollagen mRNA levels of rat hepatic stellate cells," *Acta Pharmacologica Sinica*, 22(9):793-796, 2001.

Liu et al., "Effects of the tyrosine protein kinase inhibitor genistein on the proliferation, activation of cultured rat hepatic Stellate cells," *World Journal of Gastroenterology*, 8(4):739-745, 2002.

Mann and Smart, "Transcriptional regulation of hepatic stellate cell activation," *Gut*, 50(6):891-896, 2002.

Matsui, "Differential activation of the murine laminin B1 gene promoter by RAR alpha, ROR alpha, and AP-1," *Biochemical and Biophysical Research Communications*, 220(2):405-410, 1996.

Miao et al., "Effect of acetaldehyde on Sp1 binding and activation of the mouse alpha 2(I) collagen promoter," *Archives of Biochemistry and Biophysics*, 341(1):140-152, 1997.

(Continued)

*Primary Examiner*—James (Doug) Schultz
(74) *Attorney, Agent, or Firm*—Klarquist Sparkman LLP

(57) ABSTRACT

Methods and reagents for effecting transgene expression in Hepatic Stellate Cells (HSC) comprising a 2.2 kb fragment of the promoter region of the Glial Fibrillary Acidic Protein (GFAP) gene, said construct being up-regulated by pro-fÊbronetic cytokines such as TGF-beta 1 in a dose and time dependent manner, and uses thereof.

32 Claims, 12 Drawing Sheets

OTHER PUBLICATIONS

Milliano and Luxon, "Initial signaling of the fibronectin receptor (alpha5beta 1 integrin (in hepatic stellate cells is independent of tyrosine phosphorylation," *Journal of Hepatology*, 39(1):32-37, 2003.

Olsen et al., "Converging signals synergistically activate the LAMC2 promoter and lead to accumulation of the lamin gamma 2 chain in human colon carcinoma cells," *Biochemical Journal*, 371(Pt 1):211-221, 2003.

Pieper et al., "Regulation of vimentin expression in cultured epithelial cells," *European Journal of Biochemistry*, 210(2):509-519, 1992.

Poulos et al., "Fibronectin and cytokines increase JNK, ERK, AP-1 activity and transin gene expression in rat hepatic stellate cells," *Am. J. Physiol. Gast. Liver Physiol.* 273(4, Pt 1):G804-811, 1997.

Rippe and Brenner, "From quiescence to activation: Gene regulation in hepatic stellate cells," *Gastroenterology*, 127(4):1260-1262, 2004.

Sakata et al., "Green tea polyphenol epigallocatechin-3-gallate inhibits platelet-derived growth factor-induced proliferation of human hepatic stellate cell line L190," *Journal of Hepatology*, 40(1):52-59, 2004.

Saxena et al., "Leptin induces increased alpha2(*I*) collagen gene expression in cultured rate hepatic stellate cells," *Journal of Cellular Biochemistry*, 89(2):311-320, 2003.

Segawa et al., "Antioxidant N-acetyl-L-cysteine inhibits the expression of the collagen a2(I) promoter in the activated human hepatic stellate cell line in the absence as well as the presence of transforming growth factor-b," *Hepatology Res.*, 24(2):305-315, 2002.

Shimizu and Weinstein, "Modulation of signal transduction by tea catechins and related phytochemicals," *Mutation Research: Fundamental and Molecular Mechanisms of Mutagenesis*, 591(1-2):147-160, 2005.

Tamura et al., "Molecular mechanism of fibronectin gene activation by cyclic stretch in vascular smooth muscle cells," *The Journal of Biological Chemistry*, 275(44):34619-34627, 2000.

Vergeer et al., "Interaction of Ap1, Ap2, and Sp1 with the regulatory regions of the humanpro-alpha1(I collagen gene," *Archives of Biochemistry and Biophysics*, 377(1):69-79, 2000.

Virolle et al., "Three activator protein-1 binding sites bound by the Fra-2.JunD complex cooperate for the regulation of murine laminin alpha3A (lama3A) promoter activity by transforming growth factor-beta," *The Journal of Biological Chemistry*, 273(28):17318-17325, 1998.

Yang, "Blood and urine levels of tea catechins after ingestion of different amounts of green tea by human volunteers," *Cancer Epidemiology Biomarkers & Prevention*, 7(4):351-354, 1998.

Altschul, S.F. et al., "Basic local alignment search tool", Journal of Molecular Biology, Oct. 5, 1990, pp. 403-410, vol. 215, Issue 3.

Bahr, M.J. et al., "Control of the tissue inhibitor of metalloproteinases-1 promoter in culture-activated rat hepatic stellate cells: Regulation by activator protein-1 DNA binding proteins", Hepatology, Mar. 1999, pp. 839-848, vol. 29, Issue 3.

Baroni, G.S. et al., "Interferon gamma decreases hepatic stellate cell activation and extracellular matrix deposition in rat liver fibrosis", Hepatology, May 1996, pp. 1189-1199, vol. 23, Issue 5.

Bataller, R. and Brenner, D.A., "Liver fibrosis", The Journal of Clinical Investigation, Feb. 1, 2005, pp. 209-218, vol. 115, No. 2.

Bataller, R. and Brenner, D.A., "Hepatic Stellate Cells as a Target for the Treatment of Liver Fibrosis", Seminars in Liver Disease, 2001, pp. 437-451, vol. 21, Issue 3.

Besnard, F. et al., "Multiple interacting sites regulate astrocyte-specific transcription of the human gene for glial fibrillary acidic protein", The Journal of Biological Chemistry, Oct. 5, 1991, pp. 18877-18883, vol. 266, Issue 28.

Bhunchet, E. and Wake, K., "Role of mesenchymal cell populations in porcine serum-induced rat liver fibrosis", Hepatology, Dec. 1992, pp. 1452-1473, vol. 16, Issue 6.

Brenner, D.A. et al., "Stimulation of the collagen •1(I) endogenous gene and transgene in carbon tetrachloride-induced hepatic fibrosis", Hepatology, Feb. 1993, pp. 287-292, vol. 17, Issue 2.

Brenner, M. et al., "GFAP Promoter Directs Astrocyte-specific Expression in Transgene Mice", The Journal of Neuroscience, Mar. 1994, pp. 1030-1037, vol. 14, Issue 3.

Buniatian, G. et al., "Colocalization of three types of intermediate filament proteins in perisinusoidal stellate cells: glial fibrillary acidic protein as a new cellular marker", European Journal of Cell Biology, May 1996, pp. 23-32, vol. 70, Issue 1.

Burt, A.D., "Pathobiology of hepatic stellate cells", Journal of Gastroenterology, May 1999, pp. 299-304, vol. 34, No. 3.

Campbell, J. et al., "Platelet-derived growth factor C induces liver fibrosis, steatosis, and hepatocellular carcinoma", Proceedings of the National Academy of Sciences of the United States of America, Mar. 1, 2005, pp. 3389-3394, vol. 102, Issue 9.

Cassiman, D. et al., "Synaptophysin: A Novel Marker for Human and Rat Hepatic Stellate Cells", American Journal of Pathology, Dec. 1999, pp. 1831-1839, vol. 155, No. 6.

Cassiman, D. et al., "Hepatic Stellate cell/myofibroblast subpopulations in fibrotic human and rat livers", Journal of Hepatology, Feb. 2002, pp. 200-209, vol. 36, Issue 2.

Feinstein, D.L. et al., "Isolation of cDNA clones encoding rat glial fibrillary acidic protein: expression in astrocytes and in Schwann cells", Journal of Neuroscience Research, May 1992, pp. 1-14, vol. 32, Issue 1.

Friedman, S.L. et al., "Isolated hepatic lipocytes and Kupffer cells from normal human liver: morphological and functional characteristics in primary culture", Hepatology, Feb. 1992, pp. 234-243, vol. 15, Issue 2.

Friedman, S.L., "Liver Fibrosis—from bench to bedside", Journal of Hepatology, 2003, pp. S38-53, vol. 38, Supplement S1.

Geerts, A., "On the origin of stellate cells: mesodermal, endodermal or neuro-ectodermal?", Journal of Hepatology, Feb. 2004, pp. 331-334, vol. 40, Issue 2.

Herrmann, J. et al., "CSRP2, TIMP-1, and SM22a promoter fragments direct hepatic stellate cell-specific transgene expression in vitro, but not in vivo", Liver International, Feb. 2004, pp. 69-79, vol. 24, Issue 1.

Kinoshita, K. et al., "Targeted and regutable expression of transgenes in hepatic stellate cells using an adenoviral Cre-IoxP system.", Hepatology, Oct. 2003, vol. 38 (4—Suppl. 1): 260A (Meeting Info.: 54th Annual meeting of the American Association for the Study of Liver Diseases. Boston, MA, USA. Oct. 24-28, 2003. American Association for the Study of Liver Diseases. Abstract—as cited by STN—Thomson Corp).

Levy, M. et al., "Fibroblast activation protein: A cell surface dipeptidyl peptidase and gelatinase expressed by stellate cells at the tissue remodelling interface in human cirrhosis", Hepatology, Jun. 1999, pp. 1768-1778, vol. 29, Issue 6.

Magness, S.T. et al., "A dual reporter gene transgenic mouse demonstrates heterogeneity in hepatic fibrogenic cell populations", Hepatology, Nov. 2004, pp. 1151-1159, vol. 40, Issue 5.

Maubach, G. et al. "GFAP promoter directs IaxZ expression specifically in a rat hepatic stellate cell line", World Journal of Gastroenterology, Feb. 7, 2006, pp. 723-730, vol. 12, Issue 5.

Needleman, S.B. and Wunsch, C.D., "A general method application to the search for similarities in the amino acid sequence of two proteins.", Journal of Molecular Biology, Mar. 28, 1970, pp. 443-453, vol. 48, Issue 3.

Pearson, W.R. and Lipman, D.J., "Improved tools for biological sequence comparison.", Proceedings of the National Academy of Sciences of the United States of America, Apr. 15, 1988, pp. 2444-2448, vol. 85, Issue 8.

Sato, M. et al., "Hepatic Stellate Cells: Unique Characteristics in Cell Biology and Phenotype", Cell Structure and Function, 2003, pp. 105-112, vol. 28, No. 2.

Slack, J.L. et al., "An Upstream Regulatory Region Mediates High-Level, Tissue-Specific Expression of the Human alpha1(I) Collagen Gene in Transgenic Mice", Molecular and Cellular Biology, Apr. 1991, pp. 2066-2074, vol. 11, Issue 4.

Smith, T.F. and Waterman, M.S., "Comparison of biosequences.", Advances in Applied Mathematics, Dec. 1981, pp. 482-489, vol. 2, Issue 4.

Vogel, S. et al., "An immortalized rat liver stellate cell line (HSC-T6): a new cell model for the study of retinoid metabolism in vitro.", Journal of Lipid Research, Jun. 2000, pp. 882-893, vol. 41, Issue 6.

Xu, L. et al., "Human hepatic stellate cell lines, LX-1 and LX-2: new tools for analysis of hepatic fibrosis.", Gut, Jan. 2005, pp. 142-151, vol. 54, Issue 1.

Yata, Y. et al., "Dnase I-hypersensitive sites enhance alpha1 (I) collagen gene expression in hepatic stellate cells", Hepatology, Feb. 2003, pp. 267-276, vol. 37, Issue 2.

Yokoi, Y. et al, "Immunocytochemical detection of desmin in fat-storing cells (Ito Cells)", Hepatology, 1984, pp. 709-714, vol. 4, No. 4.

Zhuo, L. et al., "Live Astrocytes Visualized by Green Fluorescent Protein in Transgenic Mice", Developmental Biology, Jul. 1, 1997, pp. 36-42, vol. 187, Issue 1.

Neubauer, K. et al., "Glial fibrillary acidic protein—a cell type specific marker for Ito cells in vivo and in vitro", Journal of Hepatology, Jun. 1996, pp. 719-730, vol. 24, Issue 6.

Niki, T. et al., "Comparison of glial fibrillary acidic protein and desmin staining in normal and CC14-induced fibrotic rat livers", Hepatology, Jun. 1996, pp. 1538-1545, vol. 23, Issue 6.

Gard, A.L. et al., "Extra-neural glial fibrillary acidic protein (GFAP) immunoreactivity in perisinusoidal stellate cells of rat liver", Journal of Neuroimmunology, 1985, pp. 359-375, vol. 8.

Segovia, J. et al., "Differentiation-dependent expression of transgenes in engineered astrocyte cell lines", Neuroscience Letters, Feb. 20, 1998, pp. 172-176, vol. 242, Issue 3.

Toru-Delbauffe, D. et al., "Effects of TGF beta 1 on the proliferation and differentiation of an immortalized astrocyte cell line: relationship with extracellular matrix", Experimental Cell Research, Oct. 1992, pp. 316-325, vol. 202, Issue 2.

Yoshida, T. and Takeuchi, M., "Establishment of an astrocyte progenitor cell line: induction of glial fibrillary acidic protein and fibronectin by transforming growth factor-beta 1", Journal of Neuroscience Research, Jun. 1, 1993, pp. 129-137, vol. 35, Issue 2.

Reilly, J.F. et al., "Regulation of astrocyte GFAP expression by TGF-beta1 and FGF-2", Glia, Feb. 1998, pp. 202-210, vol. 22, Issue 2.

deOliveira Sousa, V. et al., "Glial fibrillary acidic protein gene promoter is differently modulated by transforming growth factor-beta1 in astrocytes from distinct brain regions", European Journal of Neuroscience, Apr. 2004, pp. 1721-1730, vol. 19, Issue 7.

Weiner, F.R. et al., "Ito-cell gene expression and collagen regulation", Hepatology, Jan. 1990, pp. 111-117, vol. 11, Issue 1.

Hellerbrand, C. et al., "The role of TGFbeta1 in initiating hepatic stellate cell activation in vivo", Journal of Hepatology, Jan. 1999, pp. 77-87, vol. 30, Issue 1.

Kanzler, S. et al., "TGF-beta in liver fibrosis: an inducible transgenic mouse model to study liver fibrogenesis", American Journal of Physiology—Gatrointestinal and Liver Physiology, Apr. 1999, pp. G1059-G1068, vol. 276, Issue 4.

Muhlbauer, M. et al., "LPS-mediated NFkappaB activation varies between activated human hepatic stellate cells from different donors", Biochemical and Biophysical Research Communications, Dec. 3, 2004, pp. 191-197, vol. 325, Issue 1.

Yoshida, K. et al., "Transforming Growth Factor-{beta} and Platelet-Derived Growth Factor Signal via c-Jun N-Terminal Kinase-Dependent Smad2/3 Phosphorylation in Rat Hepatic Stellate Cells after Acute Liver Injury", The American Journal of Pathology, Apr. 2005, pp. 1029-1039, vol. 166, Issue 4.

Niki, T. et al., "Class VI intermediate filament protein nestin is induced during activation of rat hepatic stellate cells", Hepatology, Feb. 1999, pp. 520-527, vol. 29, Issue 2.

Geerts, A. et al., "Formation of normal desmin intermediate filaments in mouse hepatic stellate cells requires vimentin", Hepatology, Jan. 2001, pp. 177-188, vol. 33, Issue 1.

Baba, S. et al., "Commitment of bone marrow cells to hepatic stellate cells in mouse", Journal of Hepatology, Feb. 2004, pp. 255-260, vol. 40, Issue 2.

Sarid, J., "Identification of a cis-acting positive regulatory element of the glial fibrillary acidic protein gene", Journal of Neuroscience Research, Feb. 1991, pp. 217-228, vol. 28, Issue 2.

Masood, K. et al., "Analysis of a segment of the human glial fibrillary acidic protein gene that directs astrocyte-specific transcription", Journal of Neuroschemistry, Jul. 1993, pp. 160-166, vol. 61, Issue 1.

Zhuo, L. et al., "hGFAP-cre transgenic mice for manipulation of glial and neuronal function in vivo", Genesis, Oct. 2001, pp. 85-94, vol. 31, Issue 2.

Krohn, K. et al., "Glial Fibrillary Acidic Protein Transcription Responses to Transforming Growth Factor-b1 and Interleukin-1b Are Mediated by a Nuclear Factor-1-Like Site in the Near-Upstream Promoter", Journal of Neurochemistry, Apr. 1999, pp. 1353-1361, vol. 72, Issue 4.

Ramadori, G. and Saile, B., "Mesenchymal cells in the liver—one cell type or two?", Liver International, Aug. 2002, pp. 283-294, vol. 22, Issue 4.

Hui, A.Y. et al., "Prostaglandin E2 inhibits transforming growth factor beta 1-mediated induction of collagen alpha 1(I) in hepatic stellate cells", Journal of Hepatology, Aug. 2004, pp. 251-258, vol. 41, Issue 2.

Knittel, T. et al., "Expression patterns of matrix metalloproteinases and their inhibitors in parenchymal and non-parenchymal cells of rat liver: regulation by TNF-alpha and TGF-beta1", Journal of Hepatology, Jan. 1999, pp. 48-60, vol. 30, Issue 1.

Romanelli, R.G. et al., "Effect of pentoxifylline on the degradation of procollagen type I produced by human hepatic stellate cells in response to transforming growth factor-beta 1", British Journal of Pharmacology, Nov. 13, 1997, pp. 1047-1054, vol. 122, Issue 6.

Wang, S. et al., "Expression of Interleukin-10 by in Vitro and in Vivo Activated Hepatic Stellate Cells", The Journal of Biological Chemistry, Jan. 2, 1998, pp. 302-308, vol. 273, Issue 1.

Wong, L. et al., "Induction of •-Platelet derived Growth Factor Receptor in Rat Hepatic Lipocytes during Cellular Activation in Vivo and in Culture", The Journal of Clinical Investigation, Oct. 1, 1994, pp. 1563-1569, vol. 94, Issue 4.

Shen, H. et al., "Different effects of rat interferon alpha, beta and gamma on rat hepatic stellate cell proliferation and activation", BMC Cell Biology, 2002, 3:9.

Schwabe, R. et al., "Human hepatic stellate cells express CCR5 and RANTES to induce proliferation and migration", American Journal of Physiology—Gastrointestinal and Liver Physiology, Nov. 2003, pp. G949-G958, vol. 285, Issue 5.

Nakatani, Y. et al., "An RNA polymeras II promoter containing sequences upstream and downstream from the RNA startpoint that direct initiation of transcription from the same site", Proceedings of the National Academy of Sciences of the United States of America, Jun. 1, 1990, pp. 4289-4293, vol. 87, Issue 11.

Murphy, F.R. et al., "Inhibition of Apoptosis of Activated Hepatic Stellate Cells by Tissue Inhibitor of Metalloproteinase-1 Is Mediated via Effects on Matrix Metalloproteinase Inhibition", The Journal of Biological Chemistry, Mar. 29, 2002, pp. 11069-11076, vol. 277, Issue 13.

Lindquist, J.N. et al., "Regulation of alpha1(I) Collagen Messenger RNA Decay by Interactions with •CP at the 3'-Untranslated Region", The Journal of Biological Chemistry, May 28, 2004, pp. 23822-23829, vol. 279, Issue 22.

Kuzmanovic, M. et al., "GFAP Promoter Drives Müller Cell-Specific Expression in Transgenic Mice", Investigative Ophthalmology & Visual Science, Aug. 2003, pp. 3606-3613, vol. 44, Issue 8.

Knittel, T. et al., "Role of the Ets-1 Transcription Factor during Activation of Rat Hepatic Stellate Cells in Culture", American Journal of Pathology, Dec. 1999, pp. 1841-1848, vol. 155, Issue 6.

Knittel, T. et al., "Rat Liver Myofibroblasts and Hepatic Stellate Cells: Different Cell Populations of the Fibroblast Lineage With Fibrogenic Potential", Gastroenterology, Nov. 1999, pp. 1205-1221, vol. 117, Issue 5.

Kawada, N., "Molecular mechanism of stellate cell activation and therapeutic strategy for liver fibrosis", Comparative Hepatology, 2004, 3(Suppl 1 ): S3.

Mathurin, P. et al., "IL-10 receptor and coreceptor expression in quiescent and activated hepatic stellate cells", American Journal of Physiology—Gastrointestinal and Liver Physiology, Jan. 9, 2002, pp. G981-G990, vol. 282, Issue 1.

Response to Communication pursuant to Article 94(3) EPC, dated Aug. 14, 2009, submitted to the European Patent Office on Feb. 23, 2010, in corresponding European Patent Application No. 06748100. 2-2406.

GenBank Accession No. M67446, Version M67446.1: Human Glial Fibrillary acidic protein (GFAP), exon 1, dated Nov. 8, 1994; accessed Apr. 2, 2008 (2 pages).

* cited by examiner

C3A/CMV-*lacZ* HepG2/CMV-*lacZ* NIH/3T3/CMV-*lacZ*

C3A/GFAP-*lacZ* HepG2/GFAP-*lacZ* NIH/3T3/GFAP-*lacZ*

T6/GFAP-*lacZ*

C6/GFAP-*lacZ*

HeLa/GFAP-*lacZ*

0ng/ml TGF-ß1

0.1ng/ml TGF-ß1

1ng/ml TGF-ß1

10ng/ml TGF-ß1

HEPATIC STELLATE CELL SPECIFIC PROMOTER AND USES THEREOF

CROSS REFERENCE TO RELATED APPLICATIONS

This application claims the benefit of U.S. Provisional Application No. 60/688,733, filed Jun. 9, 2005, the contents of which are fully incorporated herein by reference.

FIELD OF THE INVENTION

This invention relates generally to methods and reagents for effecting transgene expression in a hepatic stellate cell (HSC), transgenic HSCs and to reagents for identifying compounds with anti-fibrotic properties.

BACKGROUND OF THE INVENTION

Hepatic stellate cells (HSCs), previously known as Ito cells, lipocytes, perisinusoidal cells or fat-storing cells, are a minor cell type (roughly 5-8% of total liver cells) most commonly found in the sinusoidal area of adult livers. The basic pathobiology and history of HSC discovery have been reviewed elsewhere (Burt, (1999), *J. Gastroenterol.* 34(3): 299; Sato et al. (2003), *Cell Struct Funct.* 28(2):105). The major physiological functions of HSC include fat storage, vitamin A uptake and metabolism, and the production of extracellular matrix proteins. In the past decade, HSCs have been implicated in mounting a defense during hepatic injury, and mediating hepatic fibrogenesis by over-producing pro-fibrotic cytokines and consequently extracellular matrix (ECM) molecules. HSCs are believed to play a role in the pathogenesis of a number of clinically important conditions such as, for example, hepatic fibrosis, cirrhosis, portal hypertension and liver cancer (Geerts (2004), *J. Hepatol.* 40(2): 331). Hence, HSCs have also become a target for the development of anti-fibrotic therapies (Bataller et al., (2001), *Semin Liver Dis.* 21(3):437; Bataller et al., (2005), *J. Clin Invest.* 115(2):209; Friedman (2003), *J. Hepatol.* 38 Suppl 1:S38).

Activation of HSCs is a dominant event in fibrogenesis. During activation, quiescent vitamin A storing cells are converted into proliferative, fibrogenic, proinflammatory and contractile 'myofibroblasts' (Friedman (2003), *J. Hepatol.* 38 Suppl 1:S38; Bataller et al. (2005), *J. Clin Invest.* 115(2):209; Cassiman et al. (2002), *J. Hepatol.* 36(2):200). HSC activation proceeds along a continuum that involves progressive changes in cellular function. In vivo, activated HSCs migrate and accumulate at the sites of tissue repair, secreting large amounts of ECM components and regulating ECM degradation (Cassiman et al. (2002), *J. Hepatol.* 36(2):200). HSC identity both in vitro and in vivo has been traditionally identified with antibodies. Initially, a polyclonal rabbit antibody against chicken desmin (an intermediate filament) was used to stain cells with stellate shape in liver slices and skeletal myofibrils in rat (Yokoi et al. (1984), *Hepatology.* 4:709). Additional antibodies against vimentin (another intermediate filament) and smooth muscle-alpha-actin (SMAA) were subsequently employed to study liver fibrosis in rat (Bhunchet et al. (1992), *Hepatology.* 16:1452; Baroni et al. (1996), *Hepatology.* 23(5):1189). Despite their poor tissue- and cell-specificity, these three markers (desmin, vimentin and SMAA) have remained a common battery for identifying HSCs. Glial fibrillary acidic protein (GFAP) has also been indicated to be a marker for HSCs (Buniatian et al. (1996), *Eur J Cell Biol.* 70(1):23; Levy et al. (1999), *Hepatology* 29(6):1768; Cassiman et al., (2002), *J. Hepatol.* 36(2):200; Xu et al. (2005), *Gut.* 54:142).

Cell specific promoters are of great interest to those involved in genetic engineering for their potential to drive expression of a target gene in a specific subpopulation or subset of cells either in vitro or in vivo.

Several promoters have been investigated for their ability to express a gene of interest specifically in HSCs in vitro and in vivo. These promoters include the human collagen alpha 1 (ColI; Slack et al. (1991), *Mol Cell Biol.* 11(4):2066; Brenner et al. (1993), *Hepatology* 7(2):287; Yata et al. (2003), *Hepatology* 37:267), SMAA (Magness et al. (2004), *Hepatology* 40:1151), LIM domain protein CRP2 (CSRP2), tissue inhibitor of metalloproteinase-1 (TIMP-1) and smooth muscle-specific 22-kDa protein (SM22alpha) (Bahr et al. (1999), *Hepatology* 29(3):839; Herrmann et al. (2004), *Liver International* 24: 69).

In astrocytes, a fragment of the human GFAP (hGFAP) promoter has been shown to drive expression of operatively coupled transgenes in vitro and in vivo. The activity of this promoter fragment in non-astrocytic cells has been shown to be less predictable. The promoter fragment unreliably expressed lacZ in Müller cells in transgenic mice lines, leading to the suggestion that Müller cells may require regulatory elements beyond those contained in the promoter fragment (Brenner (1994), *J Neurosci.* 14: 1030). In Schwann cells, the transcription initiation site of the endogenous GFAP promoter is 169 nucleotides upstream from the transcription initiator site in astrocytes (Feinsten et al. (1992) *J. Neurosci Res.* 32(1):1). Further, while Schwann cells are known to express endogenous GFAP, these cells are also unreliably labeled in hGFAP-LacZ transgenic mice (Zhuo (1997), *Developmental Biology* 187:36).

SUMMARY OF THE INVENTION

The inventors here report that a 2.2 kb promoter fragment from the hGFAP gene may be used to drive transgene expression in HSCs, and further that this expression is upregulated in response to pro-fibrogenic factors. These results demonstrate that the 2.2 kb promoter from the hGFAP gene is not only capable of driving HSC-specific expression, but that the promoter contains additional regulatory sequences that are responsible for the induction of transgene transcription in HSCs.

There is thus provided a method for selectively expressing a transgenic product in HSC cells. The transgenic product may be used to identify HSCs or modulate hepatic fibrosis in vitro or in vivo.

A vector containing a marker molecule operably coupled to a GFAP promoter may be useful for identifying HSCs in vivo or in vitro. Isolated transgenic HSCs comprising a transgene operably coupled to a GFAP promoter may be used in assays to study hepatic fibrogenesis, including the in vitro or in vivo screening of factors that may affect, reduce or inhibit fibrogenesis.

In one aspect, there is provided a method for expressing a transgenic product in a hepatic stellate cell, the method comprising transfecting the hepatic stellate cell with a vector comprising a glial fibrillary acidic protein promoter operably coupled to a DNA sequence encoding the transgenic product, wherein the glial fibrillary acidic protein promoter consists of the sequence set forth in SEQ. ID NO. 1, or is an allelic variant or derivative of the sequence set forth in SEQ ID NO:1.

In another aspect there is provided an isolated transgenic hepatic stellate cell, the cell comprising a transgene operably coupled to a glial fibrillary acidic protein promoter, wherein the promoter consists of the sequence set forth in SEQ ID NO:1, or a sequence that is an allelic variant or derivative of SEQ ID NO: 1.

In another aspect, there is provided a method of identifying an anti-fibrotic agent, the method comprising providing an isolated transgenic hepatic stellate cell according to the invention; detecting a first expression level of the transgene; exposing the isolated transgenic hepatic stellate cell to a test compound; detecting a second expression level of the transgene; and comparing the first expression level and the second expression level, whereby the first expression level greater than the second expression level indicates that the test compound is an anti-fibrotic reagent.

In another aspect there is provided a use of a vector comprising a DNA sequence encoding a therapeutic product operably coupled to a glial fibrillary acidic protein promoter, wherein the glial fibrillary acidic protein promoter consists of the sequence set forth in SEQ. ID NO. 1, or is an allelic variant or derivative of the sequence set forth in SEQ ID NO:1 for treating a hepatic fibrosis related disorder.

In another aspect, there is provided a use of a vector comprising a DNA sequence encoding a therapeutic product operably coupled to a glial fibrillary acidic protein promoter, wherein the glial fibrillary acidic protein promoter consists of the sequence set forth in SEQ. ID NO. 1, or is an allelic variant or derivative of the sequence set forth in SEQ ID NO: 1 for the preparation of a medicament for treating a hepatic fibrosis related disorder.

In another aspect, there is provided a pharmaceutical preparation comprising a vector comprising a sequence encoding a therapeutic product operably coupled to a glial fibrillary acidic protein promoter, wherein the glial fibrillary acidic protein promoter consists of the sequence set forth in SEQ. ID NO. 1, or is an allelic variant or derivative of the sequence set forth in SEQ ID NO: 1 for treating a hepatic fibrosis related disorder and a physiological carrier.

In yet another aspect there is provided a method of treating a hepatic fibrosis related disorder in a subject, the method comprising administering to the subject an effective amount of a transgenic HSC, wherein the transgenic HSC comprises a transgene encoding a therapeutic product, said transgene operably coupled to a glial fibrillary acidic protein promoter, and wherein said promoter consists of the sequence set forth in SEQ. ID NO. 1, or is an allelic variant or derivative of the sequence set forth in SEQ ID NO:1.

In still yet another aspect, there is provided a kit comprising a vector comprising a sequence encoding a therapeutic product operably coupled to a glial fibrillary acidic protein promoter, wherein the glial fibrillary acidic protein promoter consists of the sequence set forth in SEQ. ID NO. 1, or is an allelic variant or derivative of the sequence set forth in SEQ ID NO.1, and instructions for treating a hepatic fibrosis related disorder in a subject.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate by way of example only, embodiments of the present invention.

DETAILED DESCRIPTION

Figure 1:
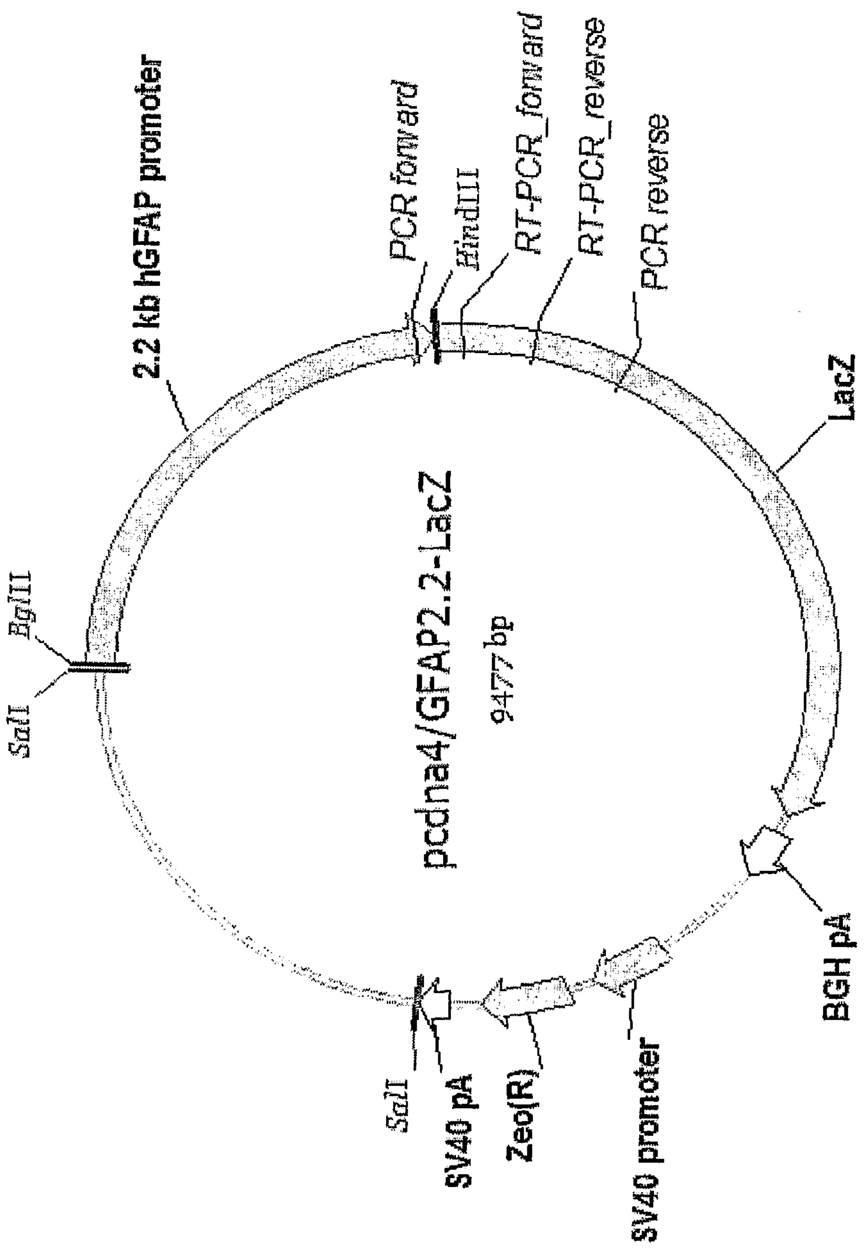
FIG. 1 depicts a map of the pcdna4/GFAP2.2-Lac Z vector.

The inventors have surprisingly discovered that a fragment of the human GFAP promoter is active in HSCs. More specifically, a 2.2 kb fragment corresponding to nucleotides −2163 to +47 (SEQ ID NO: 1) of the hGFAP gene (Accession Number M67446) is capable of driving transgene expression in rat T6 HSC cells, but not in HepG2 hepatocytes, C3A cells (a clonal derivative of HepG2) or HeLa cells. In HSC cell culture, the expression of a transgene operably coupled to a hGFAP promoter is induced in a dose-dependent manner by the pro-fibrotic factors transforming growth factor-β1 (TGF-β1), platelet derived growth factor-BB (PDGF-BB) and lipopolysaccharide (LPS).

There is presently provided a method for effecting HSC-specific transgene expression, the method comprising transfecting a HSC cell with a vector comprising a transgene operably coupled to a GFAP promoter.

As used herein, "expression" refers to any detectable level in the transcription product of a transgene in a HSC. As will be understood by a person skilled in the art, transcription levels may be determined by direct methods that measure the amount of transgene mRNA, for example, Northern Blotting or quantitative RT-PCR. Alternatively, transgene expression may be measured indirectly by measuring, the optical, coulorometric, fluorogenic, immunogenic or enzymatic properties of the protein product translated from the transgene mRNA. For example, the activity of a reporter gene, such as β-galactosidase, may be determined by known assays using the chromogenic substrate 5-Bromo-4-Chloro-3-Indolyl-BD-Galactopyranoside (X-gal). Alternatively, transgene expression may be determined by known immunological methods, for example, Western analysis.

As used herein, "transgene" refers to an exogenous DNA coding sequence. The transgene may encode a mRNA that can be translated into a protein or polypeptide product in the transfected cell. The coding region of the transgene may be contiguous or may contain one or more introns. As would be understood by a person skilled in the art, if the transgene is derived from bacteria or viral sources, the codon preference of the transgene may be optimized to that of the target HSC.

As used herein, "transfecting" refers to any process wherein exogenous nucleic acids are introduced into a HSC, and includes viral, and non-viral methods. Examples of viral methods would be known to a person skilled in the art and include, for example, the administration of lentiviral vectors. Non-viral transfection methods would also be known to the skilled person and include, for example, naked plasmids, DEAE-dextran, calcium phosphate co-precipitation, microinjection, electroporation, nucleofection (Amaxa), liposome-mediated transfection, non-liposomal lipid preparations, cationic lipids, and polycationic polymers. Many of the non-viral transfection reagents and protocols are commercially available and would be known to a person skilled in the art. In specific embodiments, transfection may be effected by Lipofectamine™ 2000 (Invitrogen) according to the directions provided by the manufacturer. In other embodiments, transfection may be effected by FuGene™ 6 (Roche) according to the directions provided by the manufacturer.

A person skilled in the art would know how to identify a transfected HSC. For example, where the transfected nucleic acid encodes a selectable marker conferring cellular resistance against a drug, transfectants may be identified by exposing cells to that drug. For example, cells transfected with a nucleic acid encoding the $Zeo^R$ selectable marker may be identified by exposing the cells to culture media containing Zeocin™. Stable transgenic HSC lines may be selected by increasing the concentration of the drug and maintaining the transfected cells at the higher drug concentrations for an appropriate period of time, which will depend, among other things, on the proliferative rate of the cells. In some instances, the stable transfected cell lines may be obtained after at least 6 weeks of drug selection.

Alternatively, where the transfected HSC expresses a fluorescent marker protein, for example, GFP or any of its fluorogenic derivatives, transfected cells may be selected by optical methods, such as, for example, fluorescent activated cell sorting (FACS) (Yata et al. (2003), *Hepatology.* 37:267). Other methods of identifying transfectants based on nucleic acid hybridization, such as, for example, southern analysis and/or PCR amplification, would be known to a person skilled in the art. As used herein, "HSC" includes a primary hepatic stellate cell (or cells) isolated from liver, as well as cells derived from the in vitro passage of primary HSCs. Methods for isolating primary HSCs would be known to a person skilled in the art, for example, those described in Friedman (1992), *Hepatology* 12:3234 and Cassiman (1999), *Am. J. Pathol.* 155(6):1831). Unless the context dictates otherwise, as used herein "HSC" includes both a quiescent and activated HSCs. Activated HSCs may be obtained by known methods, such as, for example, by culturing primary HSCs on uncoated plastic substrates.

While primary HSCs may be isolated from liver, this approach is generally limited by the low yield of HSCs, frequent presence of other cell types and the low (i.e. <1%) transfection efficiency of primary HSCs (Xu et al. (2005), *Gut.* 54:142). As used herein, "HSC" also includes model HSC-derived cell or cells, such as, for example, the immortalized rat HSC-T6 cell. Rat HSC-T6 cells exhibit an activated phenotype reflected in their fibroblast-like shape, rapid proliferation in culture and the expression of desmin, SMAA, GFAP and vimentin (Vogel et al (2000), *J Lipid Res.* 41(6):882). Other HSC-derived model cell lines would be known to a person skilled in the art and include, for example, the human LX-1 or, more preferably, the LX-2 cell lines (Xu et al. (2005), *Gut.* 54:142). Both LX-1 and LX-2 cell lines express a number of markers of activated HSC, including SMAA and GFAP, and the LX-2 line has been shown to possess a transfection efficiency exceeding 30%. HSC-T6, LX-1 and LX-2 cells may be deactivated by growth in Matrigel™ or by culture in low serum media (Xu et al. (2005), *Gut.* 54:142). In a specific embodiment, the HSC is HSC-T6.

A first nucleic acid sequence is operably coupled with a second nucleic acid sequence when the sequences are placed in a functional relationship. For example, a coding sequence is operably coupled to a promoter if the promoter activates transcription of the coding sequence. Similarly, a promoter and an enhancer are operably coupled when the enhancer increases the transcription of operably coupled sequences. Enhancers may function when separated from promoters and as such, an enhancer may be operably coupled to a promoter even though it is not contiguous to the promoter. Generally, however, operably coupled sequences are contiguous.

As would be understood by a person skilled in the art, the GFAP promoter sequence and the operably coupled transgene would generally be contained within a larger DNA vector. The vector may contain additional elements that allow for the integration, selection, replication or manipulation of the vector. For example, the vector may contain a selection marker, such as, for example, the neo and $Zeo^R$ genes, which may confer cellular resistance to G-418 and Zeocin™, respectively. Other selection markers would be known to a person skilled in art. Other additional elements would also be known to a person skilled in the art and include, for example, a multiple cloning site (MCS), and a transcription termination sequence, such as, for example, bovine growth hormone polyadenylation signal sequence (BGH pA).

The vector may be linear or circular, and, if circular, may be supercoiled. As would be known to a person skilled in the art, the efficiency of chromosomal integration may be enhanced by providing a linear vector, whereas episomal transfection may be more efficient with supercoiled DNA. Linear vectors may be prepared from circular vectors by known methods, for example, by cutting with an appropriate restriction endonuclease.

In one embodiment, the GFAP promoter is comprised of a 2.2 kb fragment corresponding to nucleotides −2163 to +47 of the hGFAP gene (Besnard et al. (1991), *J Biol Chem.* 266(28): 18877; Brenner et al. (1994), *J Neurosci.* 14: 1030; Zhuo et al. (1997), *Developmental Biology* 187:36). As detailed more fully in the accompanying examples, this 2.2 kb hGFAP promoter fragment can direct transgene expression in HSCs (but not in HepG2 or HeLa cells), and is induced by known fibrogenic factors.

In a specific embodiment, the 2.2 kb hGFAP promoter fragment has the following sequence [SEQ ID NO: 1]:

```
GAGCTCCCACCTCCCTCTCTGTGCTGGGACTCACAGAGGGAGACCTCAGG

AGGCAGTCTGTCCATCACATGTCCAAATGCAGAGCATACCCTGGGCTGGG

CGCAGTGGCGCACAACTGTAATTCCAGCACTTTGGGAGGCTGATGTGGAA

GGATCACTTGAGCCCAGAAGTTCTAGACCAGCCTGGGCAACATGGCAAGA

CCCTATCTCTACAAAAAAAGTTAAAAAATCAGCCACGTGTGGTGACACAC

ACCAGTAGTCCCAGCTATTCAGGAGGCTGAGGTGAGGGGATCACTTAAGG

CTGGGAGGTTGAGGCTGCAGTGAGTCGTGGTTGCGCCACTGCAGTCCAGC

CTGGGCAACAGTGAGACCCTGTCTCAAAAGCCAAAAAAAAAAAAAAAAAA

AAAAAGAACATATCCTGGTGTGGAGTAGGGGACGCTGCTCTGACAGAGGC

TCGGGGGCCTGAGCTGGCTCTGTGAGCTGGGGAGGAGGCAGACAGCCAGG

CCTTGTCTGCAAGCAGACCTGGCAGCATTGGGCTGGCCGCCCCCCAGGGC

CTCCTCTTCATGCCCAGTGAATGACTCACCTTGGCACAGACACAATGTTC

GGGGTGGGCACAGTGCCTGCTTCCCGCCGCACCCCAGCCCCCCTCAAATG

CCTTCCGAGAAGCCCATTGAGCAGGGGGCTTGCATTGCACCCCAGCCTGA

CAGCCTGGCATCTTGGGATAAAAGCAGCACAGCCCCCTAGGGGCTGCCCT

TGCTGTGTGGCGCCACCGGCGGTGGAGAACAAGGCTCTATTCAGCCTGTG

CCCAGGAAAGGGGATCAGGGGATGCCCAGGCATGGACAGTGGGTGGCAGG

GGGGGAGAGGAGGGCTGTCTGCTTCCCAGAAGTCCAAGGACACAAATGGG

TGAGGGGACTGGGCAGGGTTCTGACCCTGTGGGACCAGAGTGGAGGGCGT

AGATGGACCTGAAGTCTCCAGGGACAACAGGGCCCAGGTCTCAGGCTCCT

AGTTGGGCCCAGTGGCTCCAGCGTTTCCAAACCCATCCATCCCCAGAGGT

TCTTCCCATCTCTCCAGGCTGATGTGTGGGAACTCGAGGAAATAAATCTC

CAGTGGGAGACGGAGGGGTGGCCAGGGAAACGGGGCGCTGCAGGAATAAA

GACGAGCCAGCACAGCCAGCTCATGTGTAACGGCTTTGTGGAGCTGTCAA

GGCCTGGTCTCTGGGAGAGAGGCACAGGGAGGCCAGACAAGGAAGGGGTG

ACCTGGAGGGACAGATCCAGGGGCTAAAGTCCTGATAAGGCAAGAGAGTG

CCGGCCCCCTCTTGCCCTATCAGGACCTCCACTGCCACATAGAGGCCATG

ATTGACCCTTAGACAAAGGGCTGGTGTCCAATCCCAGCCCCCAGCCCCAG

AACTCCAGGGAATGAATGGGCAGAGAGCAGGAATGTGGGACATCTGTGTT

CAAGGGAAGGACTCCAGGAGTCTGCTGGGAATGAGGCCTAGTAGGAAATG
```

-continued

```
AGGTGGCCCTTGAGGGTACAGAACAGGTTCATTCTTCGCCAAATTCCCAG

CACCTTGCAGGCACTTACAGCTGAGTGAGATAATGCCTGGGTTATGAAAT

CAAAAAGTTGGAAAGCAGGTCAGAGGTCATCTGGTACAGCCCTTCCTTCC

CTTTTTTTTTTTTTTTTTTGTGAGACAAGGTCTCTCTCTGTTGCCCAGGC

TGGAGTGGCGCAAACACAGCTCACTGCAGCCTCAACCTACTGGGCTCAAG

CAATCCTCCAGCCTCAGCCTCCCAAAGTGCTGGGATTACAAGCATGAGCC

ACCCCACTCGAGCCCTTTCCTTCCTTTTTAATTGATGCATAATAATTGTA

AGTATTCATCATGGTCCAACCAACCCTTTCTTGACCCACCTTCCTAGAGA

GAGGGTCCTCTTGCTTCAGCGGTCAGGGCCCCAGACCCATGGTCTGGCTC

CAGGTACCACCTGCCTCATGCAGGAGTTGGCGTGCCCAGGAAGCTCTGCC

TCTGGGCACAGTGACCTCAGTGGGGTGAGGGGAGCTCTCCCCATAGCTGG

GCTGCGGCCCAACCCCACCCCCTCAGGCTATGCCAGGGGGTGTTGCCAGG

GGCACCCGGGCATCGCCAGTCTAGCCCACTCCTTCATAAAGCCCTCGCAT

CCCAGGAGCGAGCAGAGCCAGAGCAGGTTGGAGAGGAGACGCATCACCTC

CGCTGCTCGC.
```

In other embodiments, the GFAP promoter is any naturally occurring or engineered sequence that is an allelic variant or derivative of the 2.2 kb hGFAP sequence. As used herein, allelic variants or derivatives contemplate sequences that contain one or more nucleotide additions, substitutions and deletions while retaining the ability to direct selective transgene expression in HSC cells. For example, in different embodiments, the GFAP promoter may correspond to smaller fragments of the 2.2 kb hGFAP promoter that retain the ability to direct HSC-specific expression. Allelic variants of the hGFAP promoter also include naturally occurring homologous sequences from other organisms or allelic variants or derivatives thereof that retain the ability to direct HSC-selective transgene expression. Methods for identifying allelic variants or derivatives directing HSC-specific expression would be known to a person skilled in the art, for example, by deletion mapping.

In still other embodiments, the GFAP promoter is a recombinant hybrid promoter comprising one or more heterologous enhancer elements operably coupled to all or a portion of the 2.2 kb hGFAP promoter sequence, or an allelic variant or derivative thereof, provided the hybrid promoter is capable of selectively directing expression in a HSC. In this context, selective expression refers to a promoter that can direct the expression of an operably coupled transgene in HSCs but not in non-HSC liver cells such as, for example, hepatocytes.

The enhancer elements in the hybrid promoter may be selected from known elements, such as, for example, enhancer elements from the human cytomegalovirus, or may be novel elements identified thorough known methods, such as, for example, enhancer trap assays.

Hybrid promoters may be synthesized using standard molecular biology and molecular cloning techniques known in the art, for example, as described in Sambrook et al. (2001) Molecular Cloning: a Laboratory Manual, 3rd ed., Cold Spring Harbor Laboratory Press). As will be understood, the term "recombinant" when referring to a nucleic acid molecule or construct means that heterologous nucleic acid sequences have been recombined, such that reference to a recombinant nucleic acid molecule refers to a molecule that is comprised of nucleic acid sequences that are joined together or produced by means of molecular biological techniques.

In various embodiments, GFAP promoter variants and derivatives may be substantially homologous in that they hybridize to all or part of the hGFAP promoter under moderate or stringent conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y.). Generally, stringent conditions are selected to be about 5° C. lower than the thermal melting point for the specific sequence at a defined ionic strength and pH. Stringent hybridization may, for example, be conducted in 5×SSC and 50% formamide at 42° C. and washed in a wash buffer consisting of 0.1×SSC at 65° C. Washes for stringent hybridization may, for example, be of at least 15 minutes, 30 minutes, 45 minutes, 60 minutes, 75 minutes, 90 minutes, 105 minutes or 120 minutes or longer.

The degree of homology between sequences may also be expressed as a percentage of identity when the sequences are optimally aligned, meaning the occurrence of exact matches between the sequences. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerized implementations of these algorithms (such as GAP, BESTFIT, FASTA and TFASTA in the Wisconsin Genetics Software Package, Genetics Computer Group, Madison, Wis., U.S.A.). Sequence alignment may also be carried out using the BLAST algorithm, described in Altschul et al., 1990, *J. Mol. Biol.* 215:403-10 (using the published default settings). Software for performing BLAST analysis may be available through the National Center for Biotechnology Information (through the internet at http://www.ncbi.nlm.nih.gov/). In various embodiments, the variants and derivatives may be at least 50%, at least 80%, at least 90% or at least 95%, or at least 99% identical as determined using such algorithms. In various embodiments, the transgene may encode a marker molecule that may be useful for the identification of HSCs in vitro and/or in vivo. In various embodiments, the marker molecule is a marker protein.

A marker molecule is any molecule whose expression may be determined. The marker molecule may be a RNA, whose expression may be determined by known method based on nucleic acid hybridization, such as for example, RT-PCR. Generally, however, the marker molecule is a marker protein. As used herein, "marker protein" refers to a protein whose expression and/or subcellular localization may be readily determined, such as, for example, green fluorescent protein (GFP). DNA vectors encoding other fluorescent proteins, for example, blue, cyan, green, and yellow-green and red are commercially available (Clonetech). Other marker proteins would be known to a person skilled in the art. In different embodiments, the marker protein may be an enzyme whose expression may be readily determined by providing a specific substrate and detecting the products of enzymatic turnover. Examples of enzymatic marker proteins include, for example, β-galactosidase and luciferase. Other enzymatic marker proteins would be known to a person skilled in the art. In other embodiments, the marker protein may be any protein whose expression may be detected immunologically, for example, by providing a labeled antibody that specifically recognizes and binds the marker protein, or a fragment thereof. The antibody may be a polyclonal antibody or a monoclonal antibody and may be directly or indirectly labeled according to methods known in the art, such as, for example, labeling with a fluorescent dye and detecting expression of the marker protein by fluorescence microscopy. Other immunological-based detection methods, including, for example, immunogold staining, radiolabelling, and colourometric enzymatic precipitation would be known to a person skilled in the art. In specific embodiments, the marker protein is β-galactosidase.

In other embodiments, the transgene operably coupled to the GFAP promoter encodes a therapeutic product. As used herein, "therapeutic product" includes any expression product having clinical usefulness, such as a RNA or protein that is involved in disease prevention, treatment, or a RNA or protein that has a cell regulatory effect that is involved in disease prevention or treatment. The therapeutic product may be a polypeptide, including a protein or a peptide, a ribozyme, a siRNA, an antisense RNA or a microRNA.

The therapeutic product may have clinical usefulness in diseases or disorders caused or associated with hepatic fibrosis, including, for example, cirrhosis, hepatitis C infection, hepatitis B infection, steatohepatitis associated with alcohol or obesity, hemochromatosis, Wilson's disorder, primary biliary cirrhosis (PBC) and non-alcoholic steatohepatitis (NASH).

In various embodiments, the therapeutic product is an anti-fibrotic polypeptide. Various anti-fibrotic polypeptides would be known to a person skilled in the art. Without being limited to any particular theory, the anti-fibrotic peptide may reduce or inhibit fibrosis by: (a) reducing inflammation to avoid stimulating HSC activation, such as, for example TNF-α antagonists and interleukin-10 (IL-10); (b) directly down-regulating HSC activation, such as for example, γ-interferon and hepatocyte growth factor (HGF); (c) neutralize proliferative, fibrogenic, contractile or pro-inflammatory responses of stellate cells, such as, for example, antagonists to PDGF, FGF or TGFα, including soluble cognate receptor fragments; (d) induce HSC apoptosis such as, for example, Bcl-xL or Fas; or (e) induce ECM degradation, such as, for example, matrix metalloprotease-8 (MMP-8).

In a specific embodiment, the therapeutic product is IL-10. Other therapeutic products would be known to a person skilled in the art and include, for example, the products of the Smad 7 gene, and the product of dominant negative alleles of Smad 3, Smad 4 and TGFR. Dominant negative forms of the Smad proteins are known and may be created by serine to alanine substitutions in the phosphorylation site, for example, by replacing SSXS sites to AAXA, where X represents any amino acid. Dominant negative forms of TGFR would also be known to a person skilled in the art. Other therapeutic products include, for example, dominant negative alleles of the platelet-derived growth factor receptor (PDGFR) and Diptheria toxin.

As would be understood by a person skilled in the art, a "dominant negative allele" is an allele whose expression inhibits or reduces the biological effect of the expression product of a wild-type allele. Without being limited to any particular theory, the product of a dominant negative allele may form an inactive heteromeric complex with the product of the wild-type allele.

In other embodiments, the therapeutic product is a siRNA. siRNAs are generally double stranded 19 to 22 nucleotide sequences that can effect post-transcriptional silencing of cognate mRNAs, allowing for selective suppression of gene expression. Generally, and without being limited to any specific theory, the sequence of the siRNA therapeutic product will be complementary to a portion of the mRNA of the gene sought to be silenced. For example, the siRNA may be designed to hybridize with mRNA encoding TGF-β1. HSC cells are the most important source of TGF-β1 in liver fibrosis and inhibiting TGF-β may inhibit matrix production and accelerate its degradation (Freidman (2003), *J Hepatol.* 38 Suppl 1:S38). In other embodiments, the siRNA may be designed to hybridize against α1(I) collagen mRNA. Increased α1(I) collagen expression in HSCs has been shown to be mediated primarily through a post-transcriptional mechanism, with the half life of α1(I) collagen mRNA increasing from 1.5 hours in quiescent cells to greater than 24 hours in activated HSCs. In yet other embodiments, the siRNA may be designed to hybridize against nucleic acids encoding platelet-derived growth factor (PDGF) or extracellular matrix molecules, such as, for example, fibronectin, laminin and integrin.

Guidelines for designing siRNAs would be known to the person skilled in the art, or siRNA designed to hybridize to a specific target may be obtained commercially (Ambion, Qiagen). For example, siRNAs with a 3' UU dinucleotide overhang are often more effective in inducing RNA interference (RNAi). Other considerations in designing siRNAs would be known to a person skilled in the art.

Isolated HSCs comprising a transgene operably coupled to GFAP promoter according to various aspects of the invention are also contemplated. The transgenic HSC according to different embodiments may be used to study fibrogenesis, hepatic fibrosis or for developing anti-fibrosis gene therapies. In some embodiments, the transgenic HSC cell is a transgenic rat HSC-T6 cell and in specific embodiments the transgenic HSC cell is T6/lacZ/C1.

As used herein, "isolated" refers to transgenic HSCs in in vitro culture, in the presence or absence of other cell types.

In other embodiments, a transgenic HSC according to various aspects of the invention, other than a mouse transgenic HSC, are contemplated.

There is also presently provided a method for in vitro and/or in vivo screening for anti-fibrotic reagents, the method comprising detecting the expression levels of a transgenic marker protein operably coupled to a GFAP promoter in a transgenic HSCs in the presence and the absence of a putative anti-fibrotic agent. The two expression level are then compared and anti-fibrotic agents are identified where the expression of the marker protein is reduced or abolished in the presence of the agent. Transgene expression levels may be detected by known methods, such as, for example, by the methods described above.

Similarly, the person skilled in the art would know, or could routinely determine the concentration of the anti-fibrotic agent to be used in the screen according to the in vitro or in vivo screening method. The appropriate amount of the anti-fibrotic agent employed in the screen will depend, among other things, on the nature of the anti-fibrotic agent. A person skilled in the art would know to determine the appropriate concentration range, for example, by screening over several orders of magnitude and would appreciate that more potent anti-fibrotic agents would decrease expression levels of the transgene at lower concentrations.

In another embodiment, there is provided a method for treating a disorder characterized or caused by hepatic fibrosis including, for example, cirrhosis, portal hypertension liver cancer, hepatitis C infection, hepatitis B infection, PBC, NASH, hemochromatosis, Wilson's disorder or steatohepatitis associated with alcohol and obesity.

The method includes administering to a subject a nucleic acid encoding a therapeutic product operably coupled to a HSC-specific hGFAP promoter, according to various aspects of the invention. In specific embodiments, the hGFAP promoter is the 2.2 kb promoter fragment of SEQ ID NO:1. In certain embodiments, the therapeutic product is an anti-fibrotic molecule, and in specific embodiments is an anti-fibrotic polypeptide.

The subject is any subject in need of such treatment, including a mammal, and particularly a human subject.

To deliver the nucleic acid molecule specifically to HSCs, the nucleic acid may be delivered by methods known in the art, for example, by the hydrodynamic delivery of therapeutic genes via the afferent and efferent vessels of the liver, such as for example, the portal vein, the hepatic vein, or the bile duct.

Methods for introducing the nucleic acid molecule into mammalian cells in vivo are known, and may be used to administer the nucleic acid vector of the invention to a subject. A nucleic acid may be delivered into a HSC by direct injection of DNA, receptor mediated DNA uptake, viral-mediated transfection or non-viral lipid based transfection. The nucleic acid vector may be administered by microparticle bombardments, for example, using a commercially available "gene gun" (BioRad).

The nucleic acid molecule is administered in such amounts to achieve the desired results, for example, the expression of the therapeutic transgene in HSCs. For example, the nucleic acid may be delivered in such amounts to express sufficient amounts of the therapeutic product which functions to alleviate, mitigate, ameliorate, inhibit, stabilize, improve, prevent, including slow the progression of the disorder, the frequency of treatment and the type of concurrent treatment, if any.

To aid in administration, the nucleic acid molecule may be formulated as an ingredient in a pharmaceutical composition. The compositions may routinely contain pharmaceutically acceptable concentrations of salt, buffering agents, preservatives and various compatible carriers or diluents. For all forms of delivery, the nucleic acid molecule may be formulated in a physiological salt solution.

The proportion and identity of the pharmaceutically acceptable diluent is determined by chosen route of administration, compatibility with a nucleic acid molecule, compatibility with a live virus when appropriate, and standard pharmaceutical practice. Generally, the pharmaceutical composition will be formulated with components that will not significantly impair the biological properties of the nucleic acid. Suitable vehicles and diluents are described, for example, in Remington's Pharmaceutical Sciences (Remington's Pharmaceutical Sciences, Mack Publishing Company, Easton, Pa., USA 1985).

Solutions of the nucleic acid molecule may be prepared in a physiologically suitable buffer. Under ordinary conditions of storage and use, these preparations contain a preservative to prevent the growth of microorganisms, but that will not inactivate or degrade the nucleic acid molecule. A person skilled in the art would know how to prepare suitable formulations. Conventional procedures and ingredients for the selection and preparation of suitable formulations are described, for example, in Remington's Pharmaceutical Sciences and in The United States Pharmacopeia: The National Formulary (USP 24 NF19) published in 1999.

The forms of the pharmaceutical composition suitable for injectable use include sterile aqueous solutions or dispersion and sterile powders for the extemporaneous preparation of sterile injectable solutions or dispersions, wherein the term sterile does not extend to any live virus that may comprise the nucleic acid molecule that is to be administered. In all cases the form must be sterile and must be fluid to the extent that easy syringability exists.

In another embodiment, there is provided a method for treating a disorder characterized or caused by liver fibrosis, the method comprising administering to a subject in need thereof, a transgenic HSC according to various aspects of the invention, wherein the transgenic HSC comprises a transgene encoding a therapeutic product.

The subject is any subject suffering from a disorder characterized or caused by liver fibrosis, including, for example, cirrhosis, portal hypertension, liver cancer, hepatitis C infection, hepatitis B infection, PBC, NASH, hemochromatosis, Wilson's disorder or steatohepatitis associated with alcohol and obesity and who is in need of such treatment. The patient may be any animal, including a mammal, particularly a human.

An effective amount of transgenic HSCs may be administered to subject, using methods known in the art, including by surgical implantation or by injection in or near the subject's liver. The term "effective amount" as used herein means an amount effective, at dosages and for periods of time necessary to achieve the desired result, for example, to treat the specific disorder. The number of total transgenic HSCs to be administered will vary, depending on, among other things, the disorder or disease to be treated, the mode of administration, the age and health of the patient and the expression levels of the therapeutic product.

Kits and commercial packages containing the various nucleic acid molecule constructs described herein, including an expression vector containing a coding sequence encoding a therapeutic product operably coupled to a promoter comprising a HSC-specific GFAP promoter, or kits and commercial packages containing a pharmaceutical composition as described herein, are contemplated. Such a kit or commercial package will also contain instructions regarding use of the included nucleic acid molecule or pharmaceutical composition, for example, use to treat a hepatic-fibrosis related disorder, for example or for expressing an expression product in a HSC.

All documents referred to herein are fully incorporated by reference.

As can be understood by one skilled in the art, many modifications to the exemplary embodiments described herein are possible. Such modifications include the substitution of known equivalents for any aspect of the invention to achieve substantially the same result in substantially the same way. The invention, rather, is intended to encompass all such modification within its scope, as defined by the claims.

EXAMPLES

Materials and Methods

Construction of the 2.2 kb hGFAP-lacZ Transgene

The plasmid vector pcDNA4/TO/LacZ (Invitrogen, CA, USA) was used as a cloning backbone, providing the *E. coli* β-galactosidase coding sequence and the Zeocin resistance gene. The 2.2 kb human GFAP promoter used in this experiment was originally mapped for its astrocyte-specific expression both in vitro (Besnard et al. (1991), *J Biol Chem.* 266 (28):18877) and in vivo (Brenner et al. (1994), *J Neurosci.* 14: 1030). The CMVTetO2 promoter in the pcDNA4/TO/lacZ vector was replaced with the 2.2 kb GFAP promoter, which was excised from another transgene GFAP-GFP-S65T (Zhuo et al. (1997), *Developmental Biology* 187:36) by BglII/HindIII digest. The promoter/coding region junction sequences were verified by DNA sequencing. The resultant 9.5 kb plasmid (as depicted in FIG. 1) was designated as pcDNA4/GFAP2.2-LacZ in our vector depository.

Cell Lines and Culture Conditions

The rat HSC-T6 cell line (Vogel et al. (2000), *J Lipid Res.* 41(6):882) was a generous gift from Dr. Scott Friedman of the Mount Sinai School of Medicine in New York through Dr. Alex Hui (Chinese University of Hong Kong). The HepG2, C3A (a clonal derivative of the HepG2), HeLa and NIH/3T3 were from ATCC (American Type Culture Collection, VA, USA). The C6 was from JCRB (Japanese Collection of Research Bioresources, Osaka, Japan). All the cell culture media and reagents were purchased from Invitrogen (Carlsbad, Calif., USA), unless specified otherwise. All cell lines were routinely cultured in DMEM (Dulbecco's Modified Eagle Medium), supplemented with 10% FBS and 100 units penicillin/100 microgram streptomycin per ml (full DMEM) at 37° C. in a humidified atmosphere of 5% $CO_2$. The cells were routinely split twice a week in a 1:3 ratio by trypsinization (0.05% trypsin/0.53 mM EDTA).

Cell Transfection and Stable Selection

The T6, C6 and HeLa cells were stably transfected with 0.5-1.0 μg of the linearised plasmid vector using the Lipofectamine2000 kit, according to instructions provided by the manufacturer (Invitrogen, CA, USA). Twenty-four hours after transfection, the medium was changed and supplemented with 250-500 μg/ml Zeocin™ for selection for at least six weeks before further assays as described below are performed. The final concentration for maintaining the stable transfected cells was 500 μg/ml Zeocin™. Alternatively, HepG2, C3A and NIH/3T3 were transiently transfected with the circular plasmid using the FuGene 6 kit (Roche Diagnostics).

Genomic Detection of the Transgene

In order to confirm the transgene integrity and integration into the genome in stable transfectants, genomic DNA was isolated from cell clones stable for at least two months under 500 μg/ml Zeocin selection, using the NucleoSpin blood kit (Macherey & Nagel, Düren, Germany). A polymerase chain reaction (PCR) strategy was used to verify the structural integrity of the inserted construct(s), with a forward primer 5'-ACTCCTTCATAAAGCCCTCG-3' [SEQ ID NO: 2] (complementary to the GFAP promoter), and a reverse primer 5'-AACTCGCCGCACATCTGAACTTCAGC-3' [SEQ ID NO: 3] (complementary to the lacZ coding sequence). The Platinum PCR SuperMix High fidelity (Invitrogen, CA, USA) was used to carry out the DNA amplification on a thermal cycler (MJ Research, FL, USA). The PCR product was analyzed on a 1% agarose gel in the RunOne electrophoresis system (EmbiTec, CA, USA) in 0.5×TAE buffer. The finished gel was documented with the AlphaDigiDoc photo system (Alpha Innotech, CA, USA). The expected PCR product was 944 bp in size.

RT-PCR GFAP-lacZ Transcript

Total cellular RNA was extracted from cells grown in 6-well plates by using the NucleoSpin RNAII kit (Macherey-Nagel, Düren, Germany) following the manufacturer's instructions. The RNA concentration was determined on a ND-100 spectrophotometer (Nanodrop Technologies, DE, USA). Fifty nanograms of total RNA was used to perform a one-step RT-PCR (Qiagen, Hilden, Germany) according to the user's manual. The primers used were: forward 5'-TCAGCTTGGAGTTGATCCCGTCG-3' [SEQ ID NO: 4], reverse 5'-AACAAACGGCGGATTGACCGTAATGG-3' [SEQ ID NO: 5]. The reaction conditions were 50° C. 30 min (cDNA synthesis), 95° C. 15 min (denaturation), 94° C. 10 sec, 55° C. 10 sec, 72° C. 19 sec for 35 cycles (PCR). The product size (337 bp) was verified in a 3% agarose gel. The β-actin (332 bp) was used as a reference.

X-Gal Staining of β-Galactosidase Activity in Fixed Cells

A lacZ reporter assay kit for cell staining (InvivoGen, CA, USA) was used to detect the reporter gene activity in both stable and transient transfectants. Development of the blue end product was monitored at different time intervals (15, 30, 60, 90, and 120 minutes). The staining results were documented with a digital camera (DP12) attached to an Olympus inverted bright field microscope (IX51).

Quantitative Solution Assay of β-Galactosidase Activity in Cell Extracts

To quantify the β-galactosidase activity in cell extracts reported in FIGS. 4 to 10, an enzyme assay kit (E2000, Promega, Wis., USA) was used to measure the specific activity of β-galactosidase, according to the manufacturer's instructions in a 96-well format. Briefly, the cells were washed twice with 1×PBS buffer (pH7.4), lysed for 15 minutes at room temperature with the reporter lysis buffer, and harvested using a cell scraper. The total cell extracts were appropriately diluted (5-10 fold), and assayed for the enzyme activity. The specific β-galactosidase activity was expressed in milliunit per milliliter (mU/ml) using a standard curve established from the β-galactosidase standard (provided with the kit). The protein concentration was measured with a BCA protein assay kit (Pierce, Ill., USA), and used to further convert the specific β-galactosidase activity from mU/ml to mU/μg total cellular protein. Six independent experiments were performed for each time and concentration data point.

Treatment of Cells with TGF-β1, PDGF-BB and LPS

Cells were seeded into 12-well plates in full DMEM and 500 μg/ml Zeocin. Twelve hours prior to the cytokine treatment, medium was changed so that the cells were allowed to grow in low serum (0.5% FBS) DMEM. The cells at a confluence of 70-80% were incubated with various concentrations (0, 0.1, 1 and 10 μg/ml) of recombinant human TGF-β1, PDGF-BB (BioVision, CA, USA) and 0, 0.1, 1 and 10 μg/ml lipopolysaccharide (LPS *E. coli*, Sigma) respectively for 0, 2, 8, 16, 24, 48 and 72 hours before they were harvested for β-galactosidase activity assay and real-time RT-PCR GFAP assay.

Real-Time RT-PCR for Endogenous Rat GFAP mRNA

Total RNA was reverse transcribed to cDNA using Taqman's reverse transcription reagent (Cat. # N808-0234A total of 400 μg of RNA in 7.7 μl nuclease-free water was added to 2 μl 10× reverse transcriptase buffer, 4.4 μl 25 mM magnesium chloride, 4 μl deoxyNTP mixtures, 1 μl random hexamers, 0.4 μl RNase inhibitor and 0.5 μl reverse transcriptase (50 U/μl) in a final reaction volume of 20 μl. The reaction was performed for 10 min at 25° C. (annealing), 30 min at 48° C. (cDNA synthesis) and 5 min at 95° C. (enzyme denaturation).

Real-time quantitative PCR was carried out with an ABI 7500 Real Time PCR System (Applied Biosystems, CA, USA). One microliter of sample cDNA was used in each PCR reaction, with the housekeeping β-actin gene as a reference for normalization. The primers and probes for rat β-actin and GFAP were purchased from Taqman's assay-on-demand database. The PCR reaction was performed under a default profile consisting of 50° C. for 2 min (UNG activation), 95° C. for 10 min (enzyme denaturation) and 40 cycles of amplification (denaturation 15 seconds, annealing and extension 60 seconds).

Relative quantitation of the target mRNA was calculated using the comparative threshold cycle ($C_T$) methods as described in the User Bulletin #2 (ABI Prism 7700 Sequence Detection System). $C_T$ indicates the fractional cycle number at which the amount of amplified target reaches a fixed threshold within the linear phase of gene amplification. $\Delta C_T$, which reflects the difference between $C_{T\ target}$ and $C_{T\ \beta\text{-}actin}$, is inversely correlated to the abundance of mRNA transcripts in the samples. $\Delta C_T$ for each sample was normalized against control experiment or calibrator and expressed as $\Delta\Delta C_T$. Relative quantitation is given by $2^{-\Delta\Delta CT}$ to express the up-regulation or down-regulation of the target gene under the treatments compared to the control.

Six independent experiments were performed for each data point and three $\Delta C_T$ were measured for each experiment.

Statistical Analysis

All quantitative results were presented as mean±SE. Experimental data were analyzed using two-tailed Student's t-test assuming unequal variances. A P-value≦0.05 was considered statistically significant.

Transgenic GFAP-GFP Mice and Immunohistochemistry

The generation and genotyping of the transgenic GFAP-GFP mice were done as previously described (Zhuo (1997), *Developmental Biology* 187:36). Mice were perfused with 0.1 M phosphate buffer saline (PBS, pH 7.4) and 4% paraformaldehyde. Liver was harvested and soaked in 30% sucrose at 4° C. overnight. Then the liver was embedded for cryosectioning using a cryostat (Leica Microsystems, Germany). For GFP and GFAP immunostaining, a mouse anti-GFP monoclonal antibody (Clontech, USA) and a rabbit anti-GFAP polyclonal antibody (DakoCytomation, Denmark; Z-0334) were used. The cryosections were washed for 5 min in 0.15 M 1×PBS followed by incubating for 4 hr at 4° C. in blocking solution of PBS containing 0.1% (v/v) Triton X-100 and 10% nonimmune goat serum. The cryosections were then washed in 0.15 M 1×PBS three times, each for 15 min. The liver sections were then incubated overnight with anti-GFP antibody (1:200) and anti-GFAP antibody (1:200) in 1×PBS containing 0.01% (v/v) Triton X-100 and 1% nonimmune goat serum at 4° C. After 3×15 min rinse in 1×PBS, the sections were incubated with a goat anti-mouse IgG conjugated with FITC (Sigma Chemicals, USA) and a goat anti-rabbit IgG conjugated with Texas-red (Abcam, U.K.) at 1:100 dilution in PBS containing 0.01% (v/v) Triton X-100 and 1% nonimmune goat serum for 2 hr at room temperature. After 3×15 min rinse in 1×PBS, the sections were coverslipped in 10 μl of the fluorescence medium and photographed with a confocal laser scanning microscope (Olympus, Japan).

Results

Transient Transfection of Non-GFAP Expressing Cell Lines with GFAP-lacZ

Figure 2:
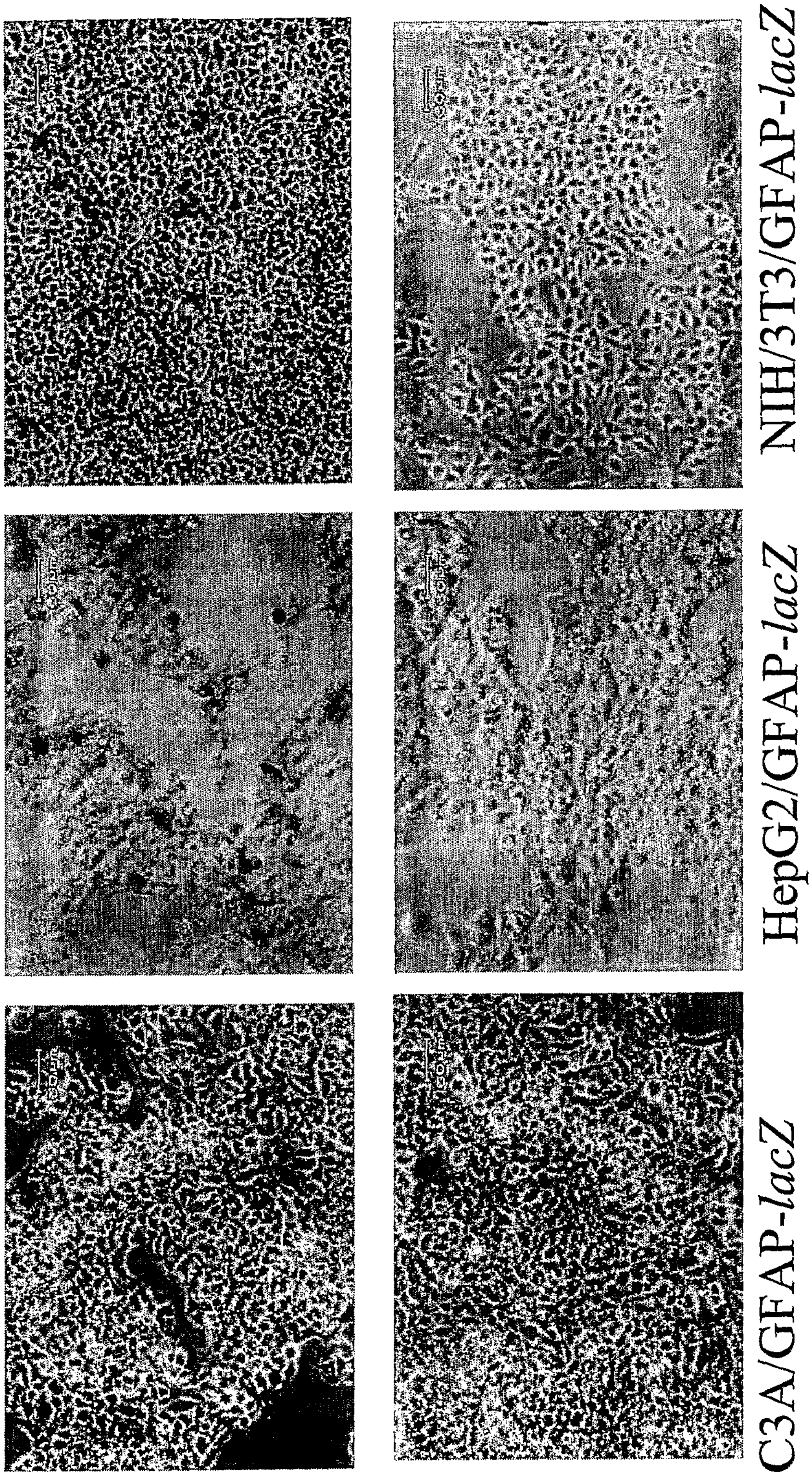
FIG. 2 depicts β-galactosidase staining in C3A, Hep2G and NIH/3T3 cells after transient transfection with vectors containing the lacZ gene under the control of a CMV promoter (top) or a GFAP promoter (bottom)

To investigate if there is any possible aberrant expression of the 2.2 kb hGFAP-lacZ transgene in several commonly used non-GFAP expressing cell types, we transiently transfected three cell lines (HepG2, C3A and NIH/3T3) with a circular form of the transgene, using a CMV-lacZ plasmid (Invitrogen) as a positive control. After the transfected cells were grown in full DMEM medium free of selection agent for two days, all three cell lines were examined for the expression of the β-galactosidase by X-gal staining method. Approximately 10-30% of the cells in each of the three lines transfected with CMV-lacZ showed blue staining (indicative of lacZ expression) after two hours of X-gal staining. In contrast, not a single cell in any of three lines transfected with the GFAP-lacZ showed any blue staining. This indicates a total lack of lacZ expression driven by the GFAP promoter in these cell lines. Representative images from two independent experiments for all three cell lines were shown in FIG. 2. After 24 hours of X-gal staining, a few cells from the HepG2 line displayed blue color in both the transfected and nontransfected groups alike (data not shown), indicative of endogenous galactosidase-like activity, which was unrelated to the transgene. No blue cells were observed in the transfected C3A and NIH/3T3.

Figure 3:
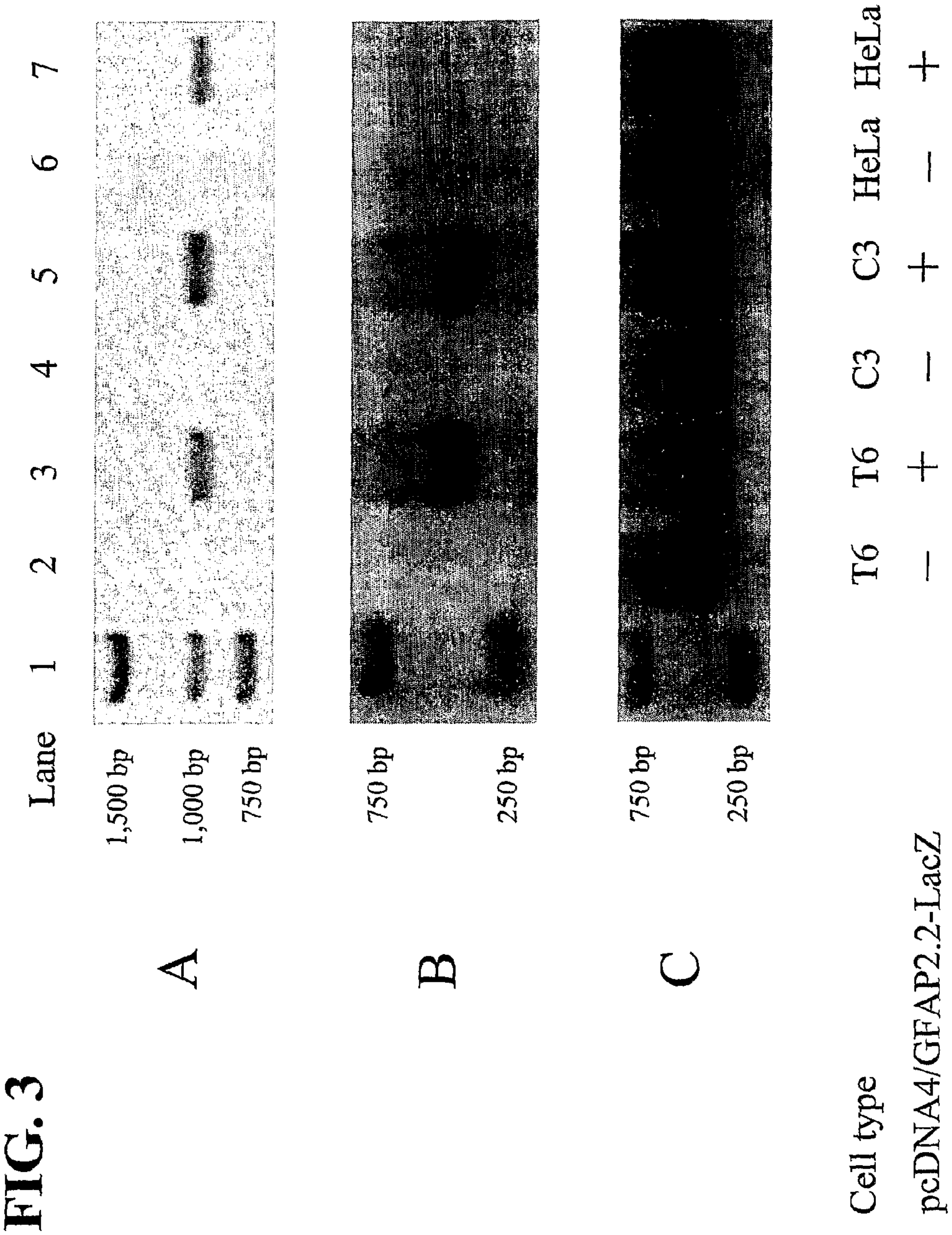
FIG. 3 depicts gel electrophoresis of PCR products from pCDNA4/GFAP2.2-LacZ transfected (lanes 3, 5, 7) and non-transfected (lanes 2, 4, 6) T6 cells (lane 2 and 3), C6 cells (lanes 4 and 5) and HeLa cells (lanes 6 and 7). Panel A depicts a GFAP-lacZ PCR products from genomic DNA. Panel B depicts LacZ RT-PCR products from 50 ng total RNA. Panel C depicts β-actin RT-PCR products. In each panel lane 1 is a 1 kb DNA ladder.
Figure 4:
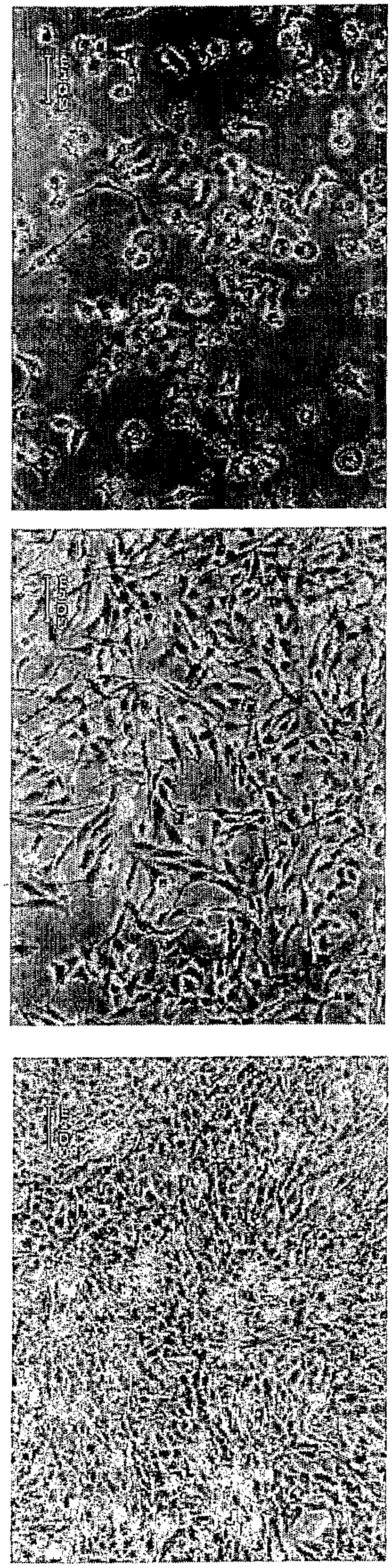
FIG. 4 depicts the β-galactosidase staining in T6, C6 and HeLa stably transfected with the 2.2 kb hGFAP-lacZ transgene.
Figure 5:
FIG. 5 depicts β-galactosidase staining in transfected T6 cells incubated with different concentrations of TGF-β1. The T6/lacZ/C1 cells were incubated with the indicated concentrations of TGF-β1 for three days prior to staining.
Figure 5:
Figure 5:
Figure 5:
Figure 6:
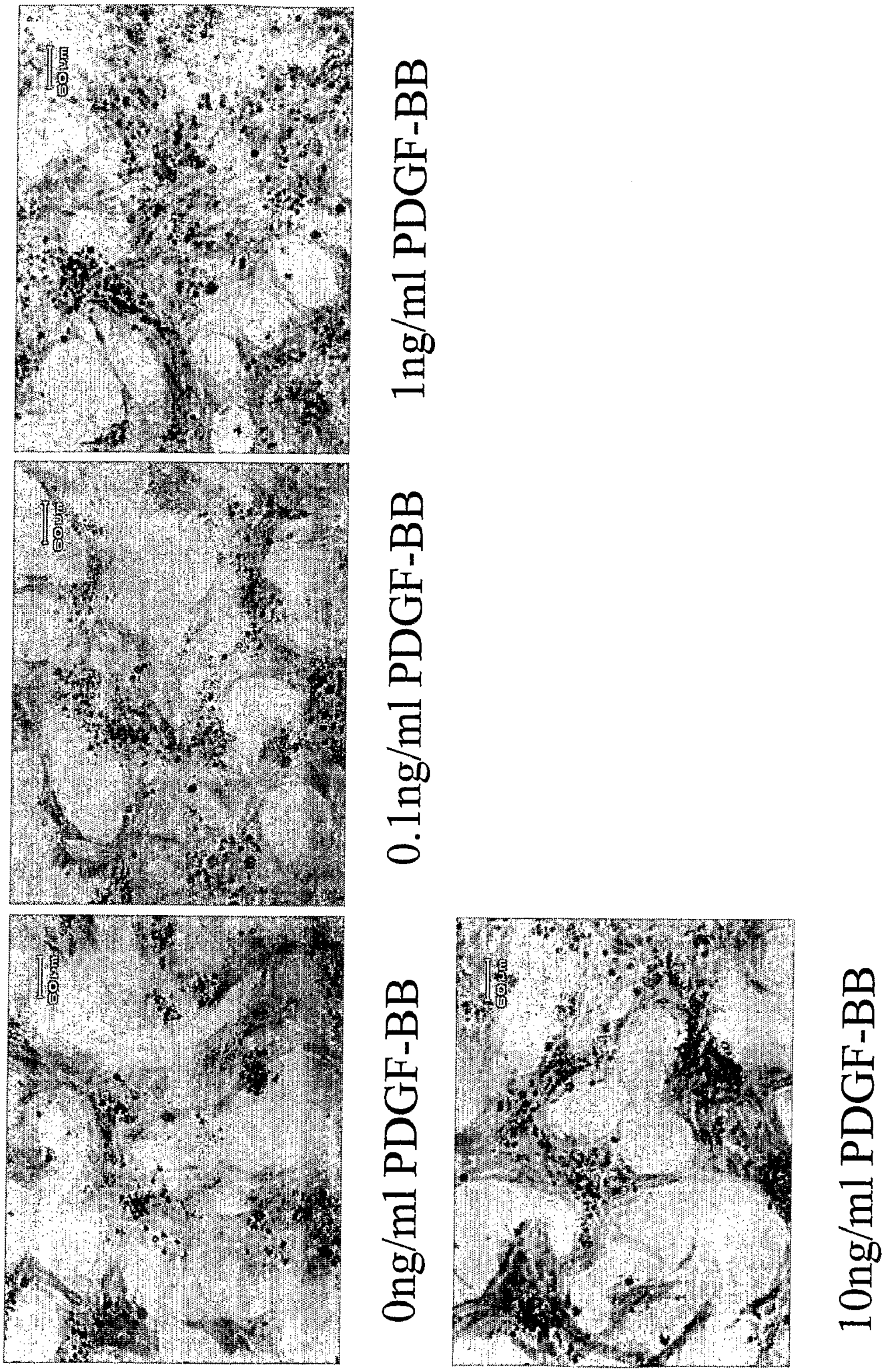
FIG. 6 depicts β-galactosidase staining in transfected T6 cells incubated with different concentrations of PDGF-BB. The T6/lacZ/C1 cells were incubated with the indicated concentrations of PDGF-BB for three days prior to staining.
Figure 7:
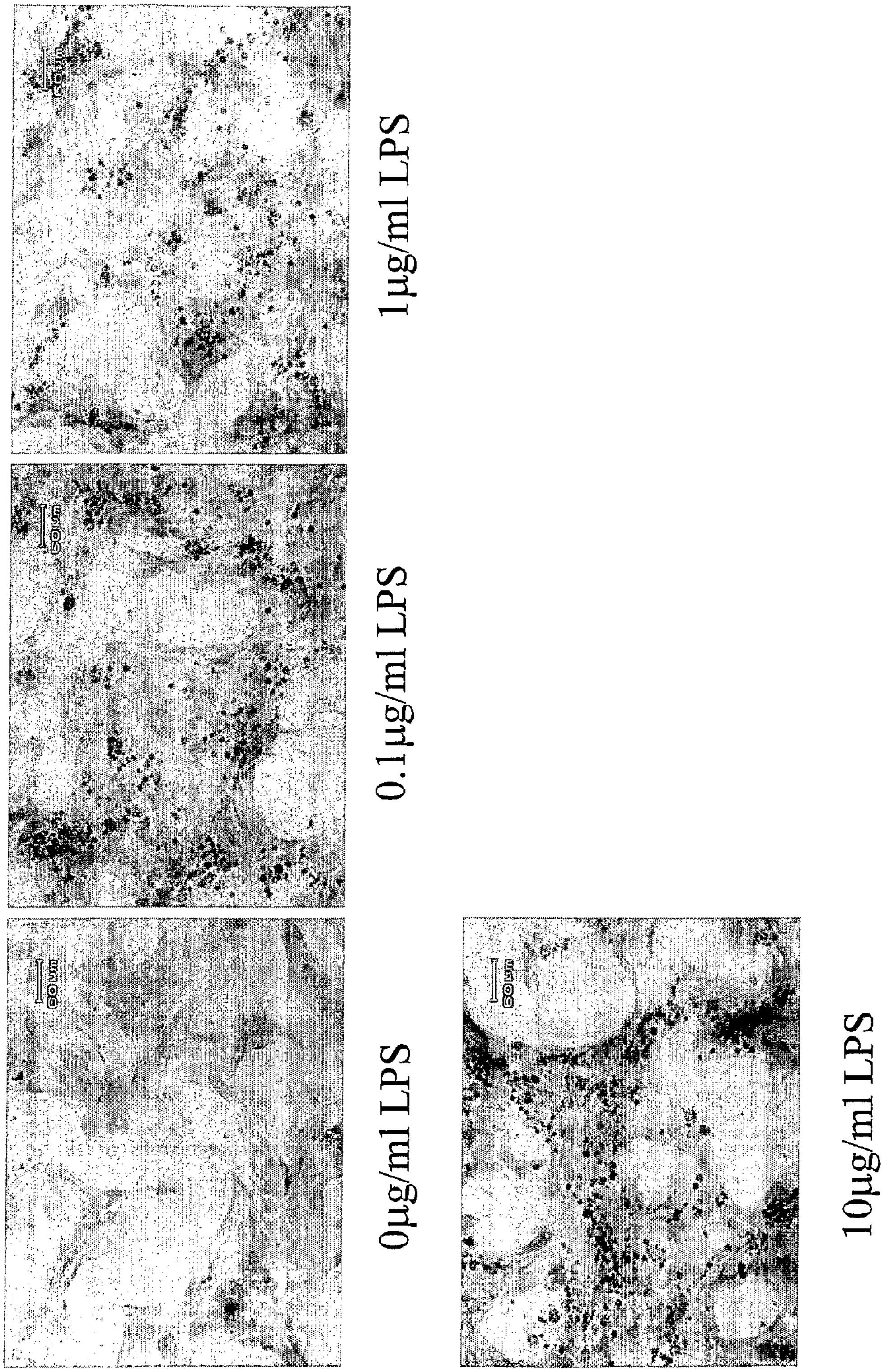
FIG. 7 depicts β-galactosidase staining in transfected T6 cells incubated with different concentrations of LPS. The T6/lacZ/C1 cells were incubated with the indicated concentrations of PDGF-BB for three days prior to staining.
Figure 8:
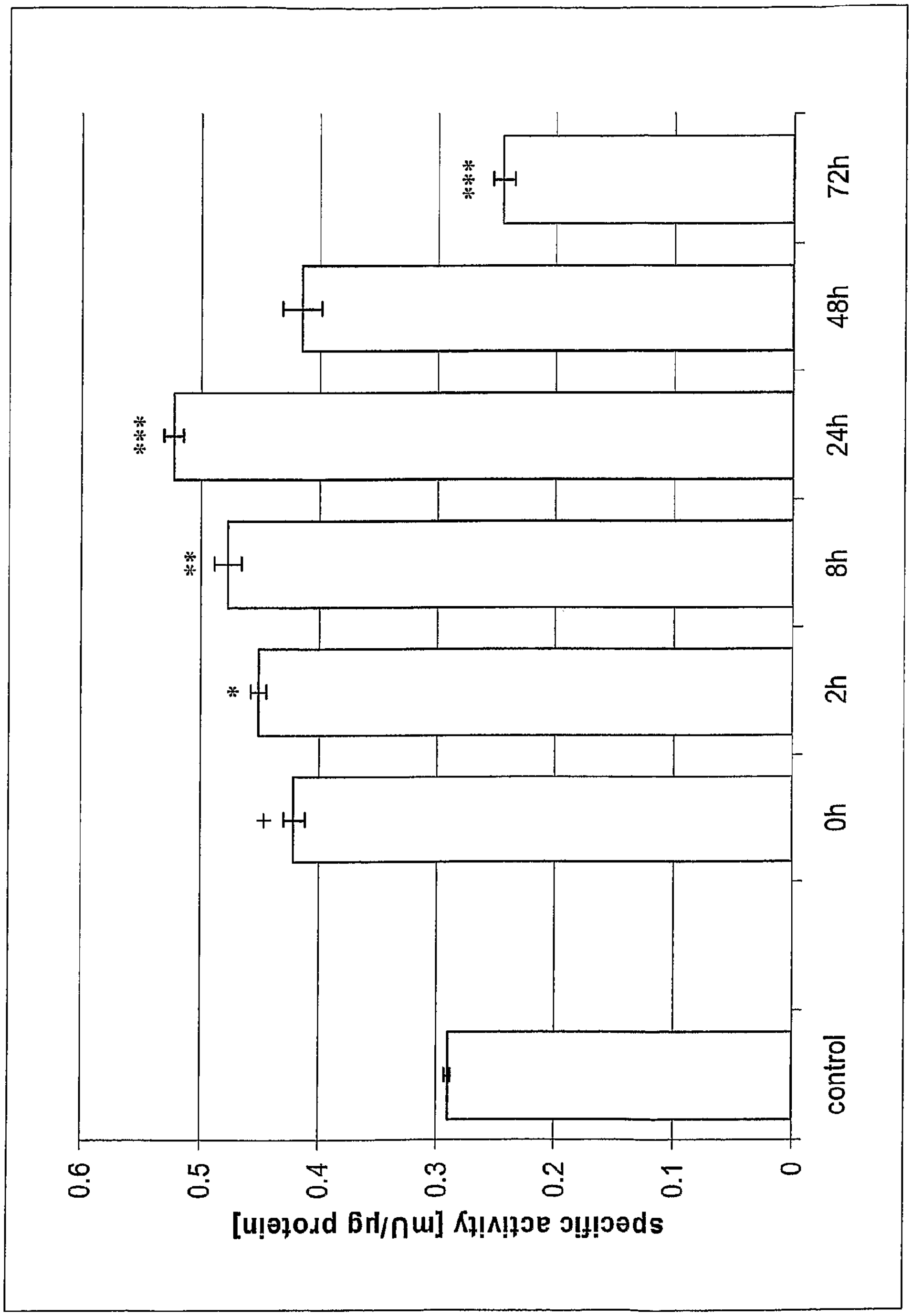
FIG. 8 depicts the β-galactosidase activity of T6/lacZ/C1 cells incubated with 1 ng/ml of the TGF-β1 as a function of incubation time. The control on the left shows the activity for the T6 stable transfected with pcDNA4/GFAP2.2-LacZ under normal growth conditions (37° C., 5% $CO_2$, 10% serum). The first data point represents the cells harvested 12 hours after changing the media to 0.5% serum. Data given as mean±SEM.+p<0.001 compared with the control; *p<0.05, p<0.005, *p<0.001 compared with the non-induced sample.
Figure 9:
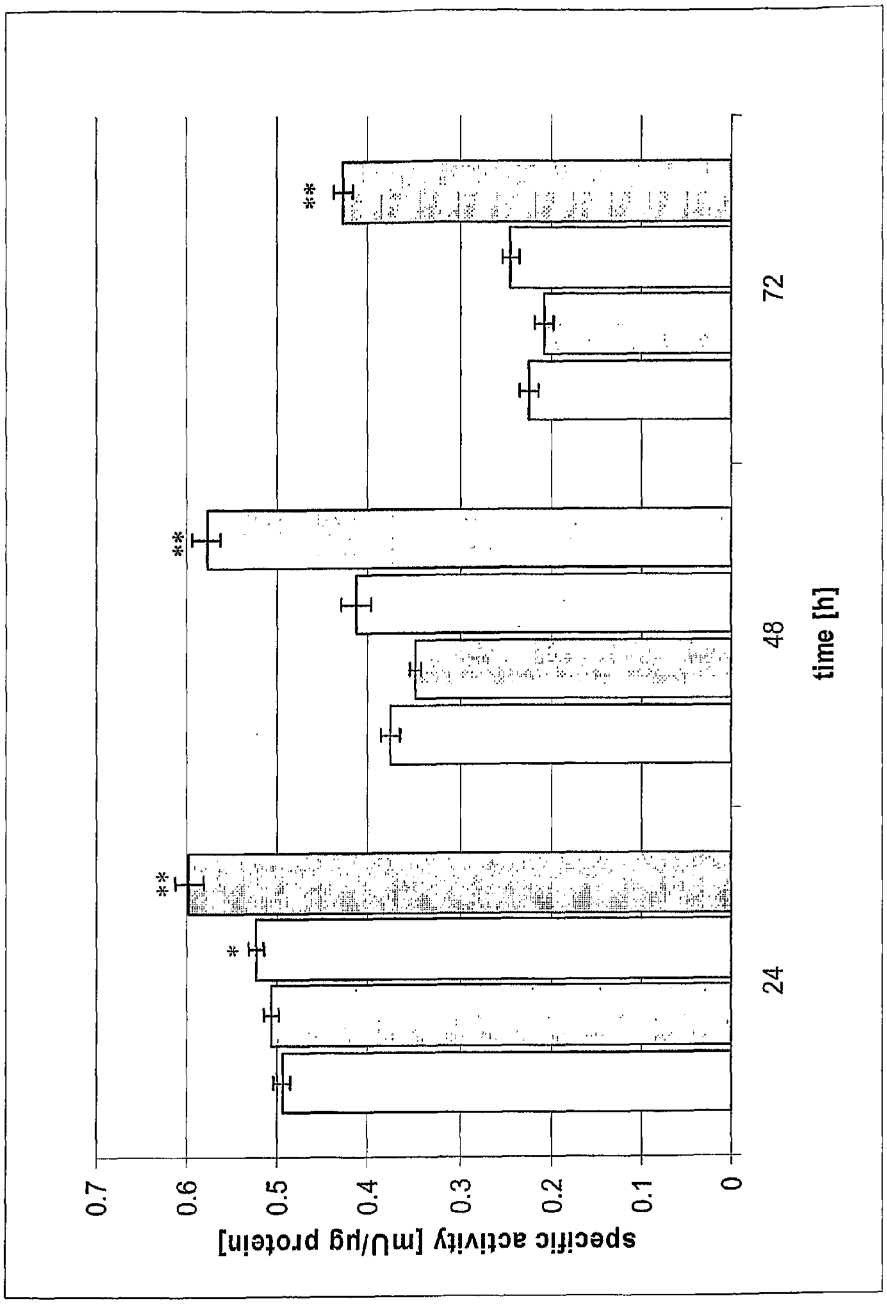
FIG. 9 depicts the time and TGF-β1 concentration dependent β-galactosidase activity of T6/lacZ1/C1 cells stably transfected with pcDNA4/GFAP2.2-LacZ. The samples were assayed for different concentrations of TGF-β1 at different time points (24, 48, 72 hours). The four columns at each time point represent the four different concentrations 0, 0.1, 1, 10 ng/ml TGF-β1 (from left to right). Data of six experiments as mean±SEM. *P<0.05, **p<0.001 compared with non-induced sample.
Figure 10:
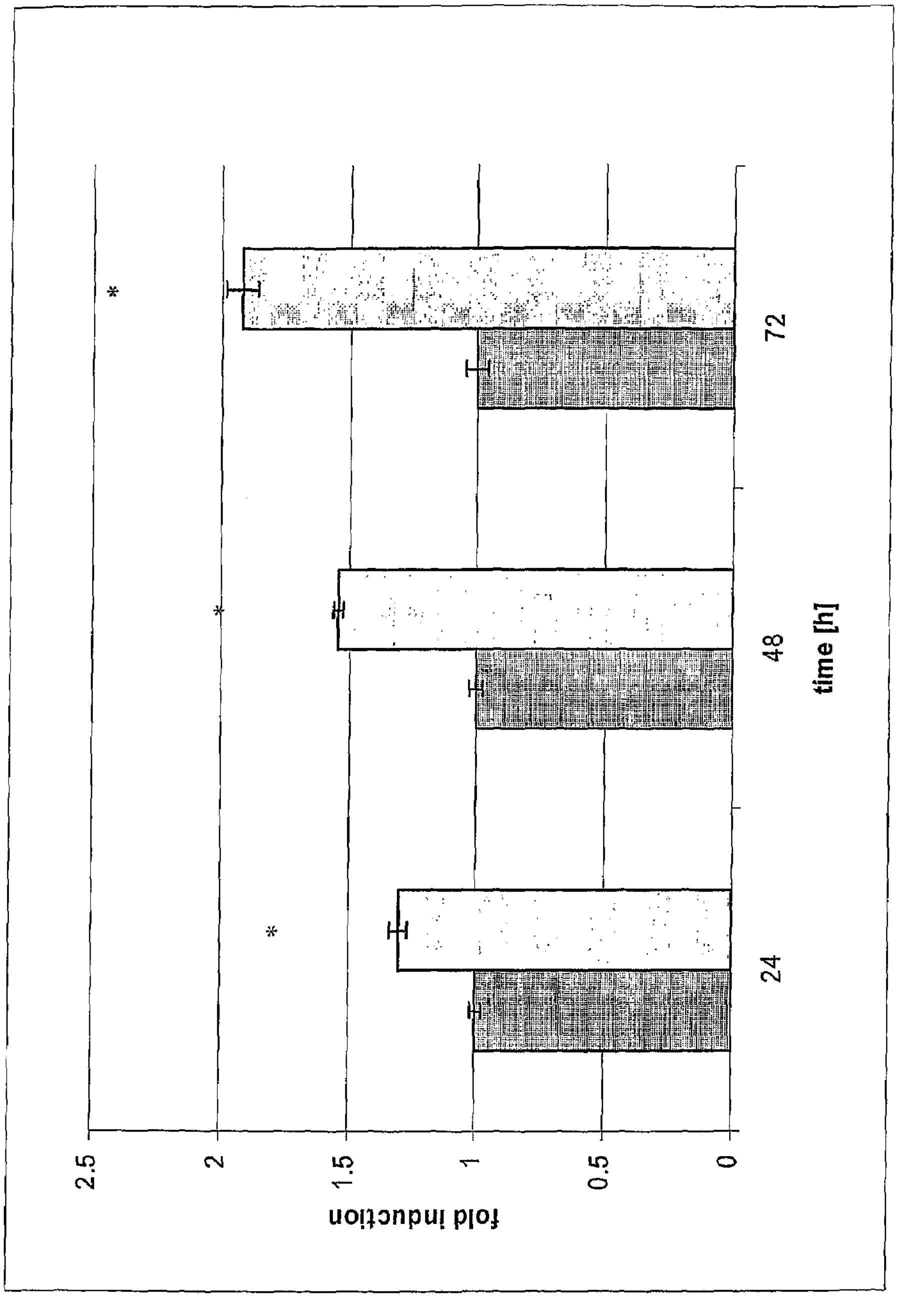
FIG. 10 depicts the inducing effect of 10 ng/ml of TGF-β1 on the fold induction of β-galactosidase specific activity under control of the GFAP 2.2 kb promoter fragment. Each induced sample was compared with its respective non-induced sample from the same experiment. The data represent the mean±SEM of six experiments. *p<0.001 compared with non-induced sample.

Stable Cell Line Transfection, Selection and Cell Specificity of Transgene Expression It was unknown whether a GFAP promoter can direct gene expression specifically in the hepatic stellate cell type. We decided to test this possibility by stably transfecting the rat hepatic stellate cell line T6 (Vogel et al. (2000), *J Lipid Res.* 41(6):882) with the GFAP-lacZ transgene, using the rat astrocyte C6 cell line and the human HeLa cell line as a positive and a negative control respectively. After selection in 250-500 mg/ml Zeocin for at least 6 weeks, several independent stable cell clones were obtained for each cell line. Subsequently, genomic DNA was isolated for analysis by PCR to check for the transgene integrity and successful integration into the host genome. PCR results confirmed the intact transgene integration in all cell lines, as evidenced by the presence of an anticipated product size of 944 bp (FIG. 3A). Furthermore, total RNA was isolated from the stable transfectants and RT-PCR was performed to verify for the lacZ transcript. The presence of a specific band with a predicted size of 337 bp indicated the lacZ transcription in the positive control C6 line, and more importantly in our target T6 line as well, but not in the negative control line HeLa (FIG. 3B). The β-actin sample is shown in FIG. 3C as a control for equal RNA loading. Next, one clone from each of the three cell lines was randomly chosen for X-gal staining for one hour. As shown in FIG. 4, the C6 and the T6 cells were positive and the HeLa was negative in blue staining. Therefore for the first time, a GFAP-based reporter gene was shown to specifically express in a hepatic stellate cell line. From this point onward, a T6 cell clone stably transfected with the 2.2 kb hGFAP-lacZ transgene (designated as T6/lacZ/C1 clone) was used for further experiments described below.

To our best knowledge, this is the first report that a GFAP promoter can direct transgene expression specifically in a hepatic stellate cell type, in a similar fashion as the endogenous GFAP does. Based on our transfection results of multiple cell types, the 2.2 kb hGFAP promoter was sufficient to confer HSC-specific, pro-fibrotic induceable expression in vitro.

X-Gal Staining of T6/lacZ/C1 Cells Treated with TGF-β1, PDGF-BB and LPS

To determine possible induction of GFAP-lacZ expression by molecules with profibrotic and proinflammatory properties in activated HSC the T6/lacZ/C1 cells were treated with TGF-β1, PDGF-BB and LPS respectively at various concentrations (0, 0.1, 1 and 10 ng/ml) in the full DMEM medium for 72 hours. The cells were then stained with X-gal for one hour and photographed. When compared to the untreated, cells treated with the profibrotic TGF-β1 (FIG. 5) and the proinflammatory LPS (FIG. 7) displayed more intense blue staining starting from 0.1 to 10 ng/ml, while the pro-proliferative PDGF-BB (FIG. 6) showed less pronounced response. In order to obtain truly quantitative data, a solution assay was employed to measure possible up-regulation of β-galactosidase activity by TGF-β1 in experiments below.

Quantitation of β-Galactosidase Activity in T6/lacZ/C1 and C6/lacZ/C4 Without Cytokine Treatment A β-galactosidase activity assay kit (Promega, Wis., USA) was used to measure transgene expression level in the T6/lacZ/C1 clone, using the nontransfected T6 as a negative basal control. When grown in the full DMEM medium to 70-80% confluence, the T6/lacZ/C1 cells yielded an average reading of approximately 0.5 mU/μg, about five times of that in normal T6 cells. The basal reading in the T6 cells was not influenced by the addition of cytokines or LPS (data not shown). For comparison purpose, the β-galactosidase activity in a randomly selected C6 clone containing the 2.2 kb hGFAP-lacZ transgene (designated as C6/lacZ/C4) was measured to have an activity of about 2 mU/μg, three times of that in the T6/lacZ/C1 cells. When incubated with TGF-β1 (0 to 10 ng/ml), the C6/lacZ/C4 cells yielded an induction dynamics of 130 to 200% of the untreated control. Under similar conditions, the T6/lacZ/C1 displayed analogous results (see data below). These data validated the use of the current assay method for quantifying transgene induction by cytokines.

Time- and Dose-Dependent β-Galactosidase Activity in Response to TGF-β1 Stimulation To quantify specific transgene response to TGF-β1, we first set up an experiment to assess possible effects that serum concentration and culture duration may have on the transgene expression. T6/lacZ/C1 cells were initially grown in DMEM with high serum (10% FBS), and then some of the cells were starved with a DMEM with low serum (0.5% FBS) for 12 hours prior to the addition of TGF-β1 (1 ng/ml). After incubation for various times (0, 2, 8, 24, 48 and 72 hours), cells were harvested for β-galactosidase activity assay. Surprisingly, the transgene expression significantly ($P<0.001$) increased from 0.29 mU/μg to 0.42 mU/μg (or a 24% increase) by simply lowering the serum concentration from 10% to 0.5% for 12 hours. After the TGF-β1 addition (to the medium with 0.5% FBS) at 0 hour, the transgene expression level was rapidly elevated at 2 and 8 hours, and eventually peaked at 24 hour, with a specific activity being 0.52 mU/μg. At 48 hours, the expression level dropped to the same level as at 0 hour. After 72 hours, the level slipped to 58% of the value at 0 hour ($P<0.001$). The assay results were depicted in FIG. 8.

To further dissect the TGF-β1 contribution to the transgene induction, we treated T6/lacZ/C1 cells grown in low serum with various concentrations of TGF-β1 (0, 0.1, 1, 10 ng/ml) and assayed the enzymatic activity for three time points (24, 48 and 72 hours). The assay results were plotted in FIG. 9. Significant induction was observed for the 10 ng/ml TGF-β1 treatment at all time points ($P<0.001$). The only other (and less) induction was seen with 1 ng/ml TGF-β1 at 24 hours ($P<0.05$). When the non-treatment groups were normalized to 1 and the magnitude of induction were plotted for the 10 ng/ml treatment groups at all three time points (FIG. 10), a trend of increasing induction with time was apparent. The most robust induction (nearly two fold) was recorded at 72 hours, though the absolute enzymatic activity (0.43 mU/μg) was the lowest among the three time points.

Time-Dependent Induction of Endogenous GFAP Transcript by TGF-β1 as Measured by Real-Time RT-PCR It was known that GFAP, along with desmin, SMAA, and vimentin, was expressed in the clonal T6 cells (Vogel et al. (2000), *J Lipid Res.* 41(6):882). Naturally, the endogenous GFAP should be expressed in the T6/lacZ/C1 cells as well. In order to investigate how the endogenous GFAP expression is regulated by TGF-β1 in the T6/lacZ/C1 cells during different time course, we quantified rat GFAP mRNA level using a real-time RT-PCR method. Cells were similarly grown and treated with TGF-β1 (1 ng/ml) for various times (0, 2, 8, 16, 24, 48 and 72 hours), as described for the enzymatic assay experiments above. Total RNA was isolated from different cells and quantified as described in Materials and Methods, and the results were depicted in FIG. 11. When compared to the basal level (normalized to 1) at 0 hour, the GFAP mRNA level remained steady within the first 24 hours, except a brief but significant suppression (0.5 fold) at 16 hour ($P<0.005$), then sharply increased to 7 and 8.5 fold of the basal level at 48 and 72 hours respectively.

Figure 11:
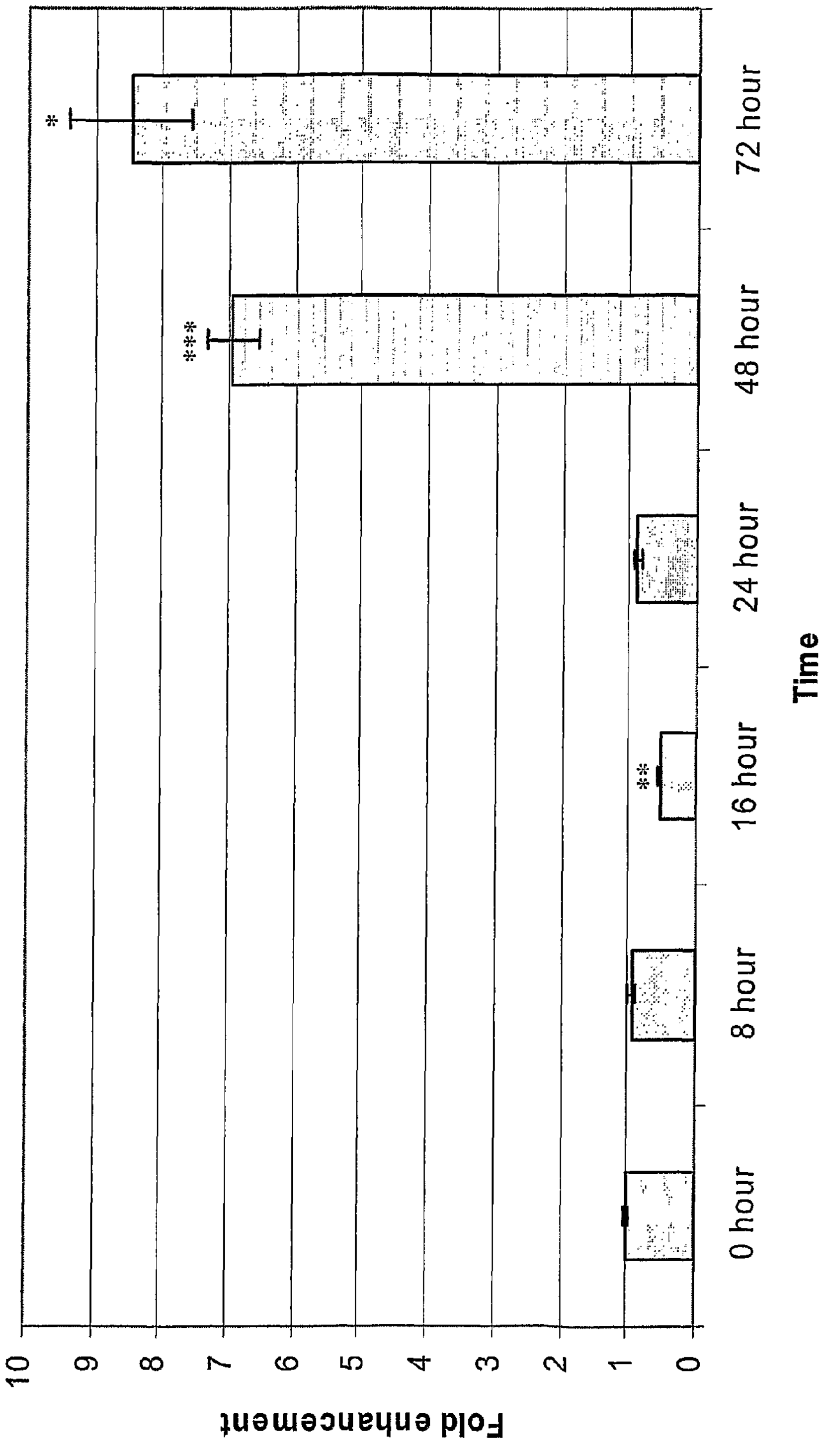
FIG. 11 demonstrates that 1 ng/ml TGF-β1 induces endogenous GFAP mRNA expression in T6/LacZ/C1 cells. *P<0.01, P<0.005, *P<0.001, compared with control.

The endogenous GFAP gene displayed a similar trend in response to TGF-β1 as the 2.2 kb GFAP-lacZ transgene did. However, two different responding features were noted between the native and the surrogate genes. First, the transgene induction was obvious even after 2 hours of incubation with TGF-β1, while the endogenous gene did not show any induction during the first 24 hours of TGF-β1 incubation. The difference in induction time line may be partially caused by the different assay detection sensitivity, presumably with the more sensitive enzymatic assay (with amplification) showing an earlier induction. Alternatively or in addition, unknown regulatory elements residing outside the 2.2 kb fragment may contribute to a more complex regulation and the observed brief decrease and delayed induction of the endogenous GFAP (FIG. 11).

As described above, the 2.2 kb hGFAP promoter is capable of expressing the lacZ reporter specifically in the rat hepatic stellate cell line T6 and responding to TGF-β1 stimulation during cell activation by up-regulation of the transgene expression. This suggests that all the cis-acting and trans-acting components and pathways needed for expression and induction of the transgene are preserved within the 2.2 kb hGFAP promoter and conserved in cultured HSCs.

Figure 12:
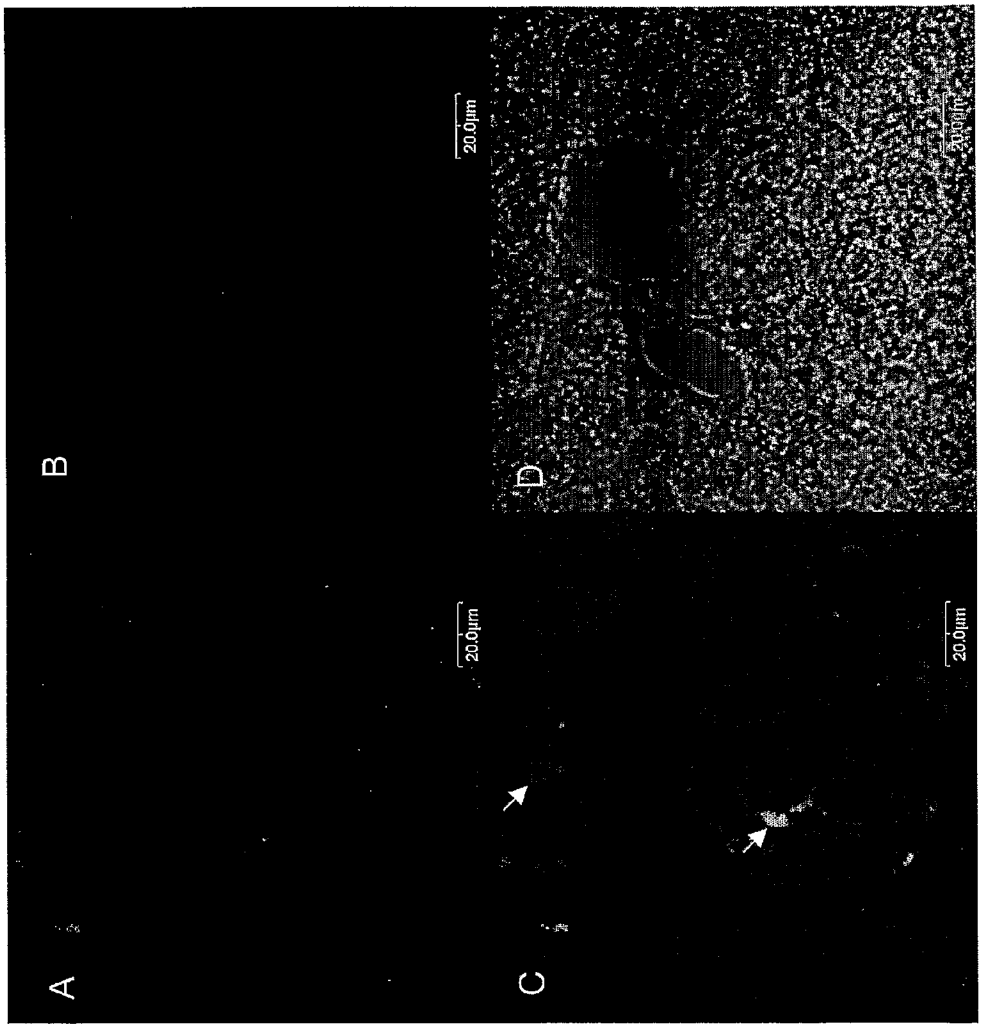
FIG. 12. The 2.21 kb hGFAP-GFP transgene was expressed specifically in the hepatic stellate cells in the liver of a transgenic mouse model. A). Liver tissue section stained with anti-GFP antibody; B) The same tissue section stained with anti-GFAP antibody; C) Merged image of A) and B); D) Light transmission of the same tissue section.

Our results (FIG. 12) demonstrate that the 2.2 kb hGFAP promoter is capable of directing HSC-specific expression in vivo by double staining the same transgenic liver tissue section with antibodies against GFAP and GFP respectively, and co-localizing on the same HSCs.

What is claimed is:

1. A method for expressing a transgenic product in a hepatic stellate cell, the method comprising transfecting the hepatic stellate cell with a vector comprising a glial fibrillary acidic protein promoter operably coupled to a DNA sequence encoding the transgenic product, wherein the glial fibrillary acidic protein promoter consists of nucleotides −2163 to +47 of a human glial fibrillary acidic protein promoter.

2. The method according to claim 1 wherein the glial fibrillary acidic protein promoter sequence consists of the sequence set forth in SEQ ID NO: 1.

3. The method according to claim 1 wherein the transgenic product is a marker molecule.

4. The method according to claim 3 wherein the marker molecule is β-galactosidase.

5. The method according to claim 1 wherein the transgenic product is a therapeutic molecule.

6. The method according to claim 5 wherein the therapeutic molecule is Smad 7, a dominant negative allele of Smad 3, Smad 4, a transforming growth factor receptor, a platelet derived growth factor receptor or a diphtheria toxin.

7. The method according to claim 5 wherein the therapeutic molecule is an anti-fibrotic polypeptide.

8. The method according to claim 7 wherein the anti-fibrotic polypeptide is interleukin-10.

9. The method according to claim 1 wherein the transgenic product is a small interfering RNA.

10. The method according to claim 9 wherein the small interfering RNA is complementary to a portion of a TGF-β1 mRNA or a portion of a platelet-derived growth factor mRNA.

11. The method according to claim 9 wherein the small interfering RNA is complementary to a portion of a mRNA encoding an extracellular matrix protein.

12. The method according to claim 11 wherein the extracellular matrix protein is collagen α1 (I), integrin, laminin or fibronectin.

13. The method according to claim 1 wherein the hepatic stellate cell is a HSC-T6, LX-1 or LX-2 cell.

14. An isolated transgenic hepatic stellate cell, the cell comprising a transgene operably coupled to a glial fibrillary acidic protein promoter, wherein the promoter consists of nucleotides −2163 to +47 of a human glial fibrillary acidic protein promoter.

15. The isolated transgenic hepatic stellate cell according to claim 14 wherein the glial fibrillary acidic protein promoter consists of the sequence set forth in SEQ ID NO: 1.

16. The isolated transgenic hepatic stellate cell according to claim 14 wherein the transgene encodes a marker molecule.

17. The isolated transgenic hepatic stellate cell according to claim 16 wherein the marker molecule is β-galactosidase.

18. The isolated transgenic hepatic stellate cell according to claim 14 wherein the transgene encodes a therapeutic molecule.

19. The isolated transgenic hepatic stellate cell according to claim 18 wherein the therapeutic molecule is Smad 7, a dominant negative allele of Smad 3, Smad 4, a transforming growth factor receptor, a platelet derived growth factor receptor or a diphtheria toxin.

20. The isolated transgenic hepatic stellate cell according to claim 18 wherein the therapeutic molecule is an anti-fibrotic polypeptide.

21. The isolated transgenic hepatic stellate cell according to claim 19 wherein the anti-fibrotic polypeptide is interleukin-10.

22. The isolated transgenic hepatic stellate cell according to claim 14 wherein the transgene encodes a small interfering RNA.

23. The isolated transgenic hepatic stellate cell according to claim 22 wherein the small interfering RNA is complementary to a portion of a TGF-β1 mRNA.

24. The isolated transgenic hepatic stellate cell according to claim 22 wherein the small interfering RNA is complementary to a portion of a collagen α1 (I) mRNA.

25. A method of identifying an anti-fibrotic agent, the method comprising:

a) providing an isolated transgenic hepatic stellate cell according to claim 18;

b) detecting a first expression level of the transgene;

c) exposing the isolated transgenic hepatic stellate cell to a test compound;

d) detecting a second expression level of the transgene; and e) comparing the first expression level and the second expression level, whereby the first expression level greater than the second expression level indicates that the test compound is an anti-fibrotic agent.

26. The method of claim 25 wherein the transgene encodes a marker molecule.

27. The method of claim 26 wherein the marker molecule is β-galactosidase.

28. A method of treating a hepatic fibrosis related disorder in a subject, the method comprising administering to the subject an effective amount of a transgenic HSC comprising a transgene encoding a therapeutic product, said transgene operably coupled to a glial fibrillary acidic protein promoter, wherein the glial fibrillary acidic protein promoter consists of nucleotides −2163 to +47 of a human glial fibrillary acidic protein promoter.

29. The method of treating a hepatic fibrosis related disorder according to claim 28, wherein the glial fibrillary acidic protein promoter consists of the sequence set forth in SEQ ID NO: 1.

30. The method according to claim 28 wherein the subject is a human subject.

31. A pharmaceutical preparation comprising a transgenic HSC, the transgenic HSC comprising a transgene encoding a therapeutic product, said transgene operably coupled to a glial fibrillary acidic protein promoter, wherein the glial fibrillary acidic protein promoter consists of nucleotides −2163 to +47 of a human glial fibrillary acidic protein promoter for treating a hepatic fibrosis related disorder.

32. The pharmaceutical preparation according to claim 31 wherein the glial fibrillary acidic protein promoter consists of the sequence set forth in SEQ ID NO: 1.

* * * * *

UNITED STATES PATENT AND TRADEMARK OFFICE

CERTIFICATE OF CORRECTION

PATENT NO. : 7,863,251 B2
APPLICATION NO. : 11/916987
DATED : January 4, 2011
INVENTOR(S) : Zhao and Maubach It is certified that error appears in the above-identified patent and that said Letters Patent is hereby corrected as shown below:

<u>In the Claims:</u>

In Column 24, line 22, “according to claim 18;” should be --according to claim 14;--.

Signed and Sealed this
Twenty-seventh Day of December, 2011

David J. Kappos
*Director of the United States Patent and Trademark Office*

SEQUENCE LISTING

<160> NUMBER OF SEQ ID NOS: 5

<210> SEQ ID NO 1
<211> LENGTH: 2208
<212> TYPE: DNA
<213> ORGANISM: Homo sapiens

<400> SEQUENCE: 1
agctcccacc tccctctctg tgctgggact cacagaggga gacctcagga ggcagtctgt 60
ccatcacatg tccaaatgca gagcataccc tgggctgggc gcagtggcgc acaactgtaa 120
ttccagcact ttgggaggct gatgtggaag gatcacttga gcccagaagt tctagaccag 180
cctgggcaac atggcaagac cctatctcta caaaaaaagt taaaaaatca gccacgtgtg 240
gtgacacaca ccagtagtcc cagctattca ggaggctgag gtgaggggat cacttaaggc 300
tgggaggttg aggctgcagt gagtcgtggt tgcgccactg cagtccagcc tgggcaacag 360
tgagaccctg tctcaaaagc caaaaaaaaa aaaaaaaaaa aaaagaacat atcctggtgt 420
ggagtagggg acgctgctct gacagaggct cgggggcctg agctggctct gtgagctggg 480
gaggaggcag acagccaggc cttgtctgca agcagacctg gcagcattgg gctggccgcc 540
ccccagggcc tcctcttcat gcccagtgaa tgactcacct tggcacagac acaatgttcg 600
gggtgggcac agtgcctgct tcccgccgca ccccagcccc cctcaaatgc cttccgagaa 660
gcccattgag caggggggctt gcattgcacc ccagcctgac agcctggcat cttgggataa 720
aagcagcaca gccccctagg ggctgccctt gctgtgtggc gccaccggcg gtggagaaca 780
aggctctatt cagcctgtgc ccaggaaagg ggatcagggg atgcccaggc atggacagtg 840
ggtggcaggg ggggagagga gggctgtctg cttcccagaa gtccaaggac acaaatgggt 900
gaggggactg ggcagggttc tgaccctgtg ggaccagagt ggagggcgta gatggacctg 960
aagtctccag ggacaacagg gcccaggtct caggctccta gttgggccca gtggctccag 1020
cgtttccaaa cccatccatc cccagaggtt cttcccatct ctccaggctg atgtgtggga 1080
actcgaggaa ataaatctcc agtgggagac ggaggggtgg ccagggaaac ggggcgctgc 1140
aggaataaag acgagccagc acagccagct catgtgtaac ggctttgtgg agctgtcaag 1200
gcctggtctc tgggagagag gcacagggag gccagacaag gaaggggtga cctggaggga 1260
cagatccagg ggctaaagtc ctgataaggc aagagagtgc cggccccctc ttgccctatc 1320

-continued

```
aggacctcca ctgccacata gaggccatga ttgaccctta gacaaagggc tggtgtccaa   1380

tcccagcccc cagccccaga actccaggga atgaatgggc agagagcagg aatgtgggac   1440

atctgtgttc aagggaagga ctccaggagt ctgctgggaa tgaggcctag taggaaatga   1500

ggtggccctt gagggtacag aacaggttca ttcttcgcca aattcccagc accttgcagg   1560

cacttacagc tgagtgagat aatgcctggg ttatgaaatc aaaaagttgg aaagcaggtc   1620

agaggtcatc tggtacagcc cttccttccc tttttttttt ttttttttgt gagacaaggt   1680

ctctctctgt tgcccaggct ggagtggcgc aaacacagct cactgcagcc tcaacctact   1740

gggctcaagc aatcctccag cctcagcctc ccaaagtgct gggattacaa gcatgagcca   1800

ccccactcag ccctttcctt cctttttaat tgatgcataa taattgtaag tattcatcat   1860

ggtccaacca accctttctt gacccacctt cctagagaga gggtcctctt gcttcagcgg   1920

tcagggcccc agacccatgg tctggctcca ggtaccacct gcctcatgca ggagttggcg   1980

tgcccaggaa gctctgcctc tgggcacagt gacctcagtg gggtgagggg agctctcccc   2040

atagctgggc tgcggcccaa ccccaccccc tcaggctatg ccaggggtg ttgccagggg   2100

cacccgggca tcgccagtct agcccactcc ttcataaagc cctcgcatcc caggagcgag   2160

cagagccaga gcaggttgga gaggagacgc atcacctccg ctgctcgc                2208


<210> SEQ ID NO 2
<211> LENGTH: 20
<212> TYPE: DNA
<213> ORGANISM: artificial sequence
<220> FEATURE:
<223> OTHER INFORMATION: synthetic primer

<400> SEQUENCE: 2

actccttcat aaagccctcg                                                  20


<210> SEQ ID NO 3
<211> LENGTH: 26
<212> TYPE: DNA
<213> ORGANISM: artificial sequence
<220> FEATURE:
<223> OTHER INFORMATION: synthetic primer

<400> SEQUENCE: 3

aactcgccgc acatctgaac ttcagc                                           26


<210> SEQ ID NO 4
<211> LENGTH: 23
<212> TYPE: DNA
<213> ORGANISM: artificial sequence
<220> FEATURE:
<223> OTHER INFORMATION: synthetic primer

<400> SEQUENCE: 4

tcagcttgga gttgatcccg tcg                                              23


<210> SEQ ID NO 5
<211> LENGTH: 26
<212> TYPE: DNA
<213> ORGANISM: artificial sequence
<220> FEATURE:
<223> OTHER INFORMATION: synthetic primer

<400> SEQUENCE: 5

aacaaacggc ggattgaccg taatgg                                           26
```